United States Patent
Bridgeman et al.

(10) Patent No.: US 11,511,086 B2
(45) Date of Patent: Nov. 29, 2022

(54) ELUTING PERFUSION CATHETERS AND RELATED METHODS

(71) Applicant: Teleflex Life Sciences Limited, Valletta (MT)

(72) Inventors: John Bridgeman, Minneapolis, MN (US); Peter Jacobs, St. Louis Park, MN (US); Dean Peterson, Minneapolis, MN (US); Joshua Brenizer, Oak Grove, MN (US); Loic Van Horne, Minneapolis, MN (US)

(73) Assignee: Teleflex Life Sciences Limited, Valletta (MT)

( * ) Notice: Subject to any disclaimer, the term of this patent is extended or adjusted under 35 U.S.C. 154(b) by 735 days.

(21) Appl. No.: 16/540,844

(22) Filed: Aug. 14, 2019

(65) Prior Publication Data

US 2020/0054865 A1    Feb. 20, 2020

Related U.S. Application Data

(60) Provisional application No. 62/719,000, filed on Aug. 16, 2018.

(51) Int. Cl.
*A61M 25/10* (2013.01)

(52) U.S. Cl.
CPC ........ *A61M 25/10* (2013.01); *A61M 25/1002* (2013.01); *A61M 25/1018* (2013.01);
(Continued)

(58) Field of Classification Search
CPC .... A61M 2025/105; A61M 2025/1045; A61M 25/1002
See application file for complete search history.

(56) References Cited

U.S. PATENT DOCUMENTS 4,762,130 A    8/1988 Fogarty et al.
4,790,315 A *  12/1988 Mueller, Jr ........... A61M 25/10
                                                    604/915
(Continued)

FOREIGN PATENT DOCUMENTS

CN    108325050 A    7/2018
EP    2689789 A1     1/2014
(Continued)

OTHER PUBLICATIONS

PCT partial international search report dated Dec. 6, 2019, in PCT application No. PCT/US2019/046545.
(Continued)

*Primary Examiner* — Nathan R Price
*Assistant Examiner* — Melissa A Snyder
(74) *Attorney, Agent, or Firm* — Robert B. Madden; Gregory W. Smock

(57) ABSTRACT

This patent document discloses perfusion catheters and related methods for treating blood vessel lesions and abnormalities. A perfusion catheter can include an inflatable balloon, an elongate shaft operably attached to the balloon, and an optional containment structure surrounding at least a portion of the balloon. The balloon can be inflated until its outer surface contacts a wall of a blood vessel. When inflated, the balloon's inner surface defines a passage for blood to flow. The balloon can be configured to release one or more substances formulated to treat a tissue at or near the wall of a blood vessel. In an example, the balloon can include a bioactive layer, which comprises the one or more substances, overlaying an optional base layer. In an example, the balloon can include multiple filars, at least one of which is configured to elute the one or more substances through a perforation or hole in the filar.

20 Claims, 14 Drawing Sheets

(52) U.S. Cl.
CPC ............... *A61M 2025/105* (2013.01); *A61M 2025/1081* (2013.01); *A61M 2210/12* (2013.01)

(56) References Cited

U.S. PATENT DOCUMENTS

| | | | |
|---|---|---|---|
| 4,909,252 A | 3/1990 | Goldberger | |
| 4,944,745 A | 7/1990 | Sogard et al. | |
| 5,047,045 A | 9/1991 | Arney et al. | |
| 5,087,247 A | 2/1992 | Horn et al. | |
| 5,181,911 A | 1/1993 | Shturman | |
| 5,195,969 A | 3/1993 | Wang et al. | |
| 5,226,888 A | 7/1993 | Arney | |
| 5,226,889 A | 7/1993 | Sheiban | |
| 5,252,159 A | 10/1993 | Arney | |
| 5,257,974 A | 11/1993 | Cox | |
| 5,295,995 A | 3/1994 | Kleiman | |
| 5,368,566 A | 11/1994 | Crocker | |
| 5,370,691 A | 12/1994 | Samson | |
| 5,421,826 A | 6/1995 | Crocker et al. | |
| 5,439,445 A | 8/1995 | Kontos | |
| 5,470,314 A | 11/1995 | Walinsky | |
| 5,505,702 A | 4/1996 | Arney | |
| 5,536,250 A | 7/1996 | Klein et al. | |
| 5,545,135 A | 8/1996 | Iacob et al. | |
| 5,545,138 A | 8/1996 | Fugoso et al. | |
| 5,549,551 A * | 8/1996 | Peacock, III | A61M 25/104 604/103.05 |
| 5,549,552 A | 8/1996 | Peters et al. | |
| 5,554,119 A | 9/1996 | Harrison et al. | |
| 5,556,382 A | 9/1996 | Adams | |
| 5,558,642 A | 9/1996 | Schweich et al. | |
| 5,569,184 A | 10/1996 | Crocker et al. | |
| 5,613,948 A | 3/1997 | Avellanet | |
| 5,643,171 A | 7/1997 | Bradshaw et al. | |
| 5,649,978 A | 7/1997 | Samson | |
| 5,683,451 A | 11/1997 | Lenker et al. | |
| 5,690,642 A | 11/1997 | Osborne et al. | |
| 5,716,340 A | 2/1998 | Schweich et al. | |
| 5,720,723 A | 2/1998 | Adams | |
| 5,738,667 A | 4/1998 | Solar | |
| 5,800,450 A | 9/1998 | Lary et al. | |
| 5,855,546 A | 1/1999 | Hastings et al. | |
| 5,879,369 A | 3/1999 | Ishida | |
| 5,882,290 A | 3/1999 | Kume | |
| 5,891,154 A | 4/1999 | Loeffler | |
| 5,961,490 A | 10/1999 | Adams | |
| 5,985,307 A * | 11/1999 | Hanson | A61M 25/0021 604/523 |
| 6,083,215 A | 7/2000 | Milavetz | |
| 6,110,097 A | 8/2000 | Hastings et al. | |
| 6,187,014 B1 | 2/2001 | Goodin et al. | |
| 6,190,355 B1 | 2/2001 | Hastings | |
| 6,245,040 B1 | 6/2001 | Inderbitzen et al. | |
| 6,361,529 B1 | 3/2002 | Goodin et al. | |
| 6,503,224 B1 | 1/2003 | Forman et al. | |
| 6,506,180 B1 | 1/2003 | Lary | |
| 6,673,040 B1 | 1/2004 | Samson et al. | |
| 6,945,957 B2 | 9/2005 | Freyman | |
| 7,147,655 B2 | 12/2006 | Chermoni | |
| 7,563,247 B2 | 7/2009 | Maguire et al. | |
| 8,049,061 B2 * | 11/2011 | Ehrenreich | A61L 29/16 604/103.08 |
| 8,430,845 B2 | 4/2013 | Wahr et al. | |
| 8,469,925 B2 | 6/2013 | Rowe et al. | |
| 8,486,014 B2 | 7/2013 | Kelly et al. | |
| 9,968,763 B2 | 5/2018 | Root et al. | |
| 10,159,821 B2 | 12/2018 | Root et al. | |
| 10,864,355 B2 | 12/2020 | Root et al. | |
| 11,027,102 B2 | 6/2021 | Peterson et al. | |
| 2002/0077591 A1 * | 6/2002 | Happ | A61F 2/958 604/96.01 |
| 2002/0151880 A1 | 10/2002 | Lafontaine | |
| 2003/0032920 A1 | 2/2003 | Wantink | |
| 2003/0040704 A1 | 2/2003 | Dorros et al. | |
| 2003/0120208 A1 | 6/2003 | Houser et al. | |
| 2003/0233068 A1 | 12/2003 | Jayaraman | |
| 2004/0093008 A1 | 5/2004 | Zamore | |
| 2004/0142704 A1 | 7/2004 | Scholz | |
| 2004/0230178 A1 | 11/2004 | Wu | |
| 2005/0075662 A1 | 4/2005 | Pedersen et al. | |
| 2006/0142704 A1 | 6/2006 | Lentz | |
| 2006/0210605 A1 | 9/2006 | Chang et al. | |
| 2006/0259062 A1 | 11/2006 | Konstantino | |
| 2008/0200896 A1 | 8/2008 | Shmulewitz et al. | |
| 2009/0105641 A1 | 4/2009 | Nissl | |
| 2011/0009818 A1 | 1/2011 | Goff | |
| 2011/0264039 A1 | 10/2011 | Thielen et al. | |
| 2012/0232640 A1 | 9/2012 | Horvers | |
| 2012/0245520 A1 | 9/2012 | Kelly et al. | |
| 2013/0018448 A1 | 1/2013 | Folan et al. | |
| 2013/0261729 A1 | 10/2013 | Gillick et al. | |
| 2015/0032148 A1 | 1/2015 | Golan | |
| 2015/0250577 A1 | 9/2015 | Hall | |
| 2015/0272732 A1 | 10/2015 | Tilson et al. | |
| 2016/0066932 A1 * | 3/2016 | Root | A61B 17/1204 606/194 |
| 2017/0143355 A1 | 5/2017 | Nicholson et al. | |
| 2019/0083760 A1 | 3/2019 | Root et al. | |
| 2020/0023169 A1 | 1/2020 | Peterson et al. | |
| 2021/0260347 A1 | 8/2021 | Peterson et al. | |

FOREIGN PATENT DOCUMENTS

| | | |
|---|---|---|
| EP | 3125781 B1 | 11/2018 |
| EP | 3400886 A1 | 11/2018 |
| JP | H09164191 A | 6/1997 |
| JP | 2002503986 A | 2/2002 |
| JP | 2005230579 A | 9/2005 |
| JP | 2011505918 A | 3/2011 |
| JP | 6097447 B2 | 3/2017 |
| JP | 6326517 B2 | 4/2018 |
| WO | 1993007929 A1 | 4/1993 |
| WO | 1994026206 A1 | 11/1994 |
| WO | 1997032626 A2 | 9/1997 |
| WO | 1998055179 A1 | 12/1998 |
| WO | 2000023139 A1 | 4/2000 |
| WO | 2005027995 A2 | 3/2005 |
| WO | 2012037507 A1 | 3/2012 |
| WO | 2014055547 A1 | 4/2014 |
| WO | 2016040579 A1 | 3/2016 |
| WO | 2017139357 A1 | 8/2017 |

OTHER PUBLICATIONS

European Search Report and Search Opinion dated Oct. 12, 2018, in European application EP18177601.4.
International Search Report dated Nov. 24, 2015, from PCT application PCT/US2015/049356 filed Sep. 10, 2015.
Written Opinion dated Nov. 24, 2015, from PCT application PCT/US2015/049356 filed Sep. 10, 2015.
PCT International Search Report dated Dec. 6, 2019, in PCT application No. PCT/US2019/046545.
PCT Written Opinion dated Dec. 6, 2019, in PCT application No. PCT/US2019/046545.
European Search Report dated Jan. 1, 2020, in EP application No. 19178585.6.

* cited by examiner

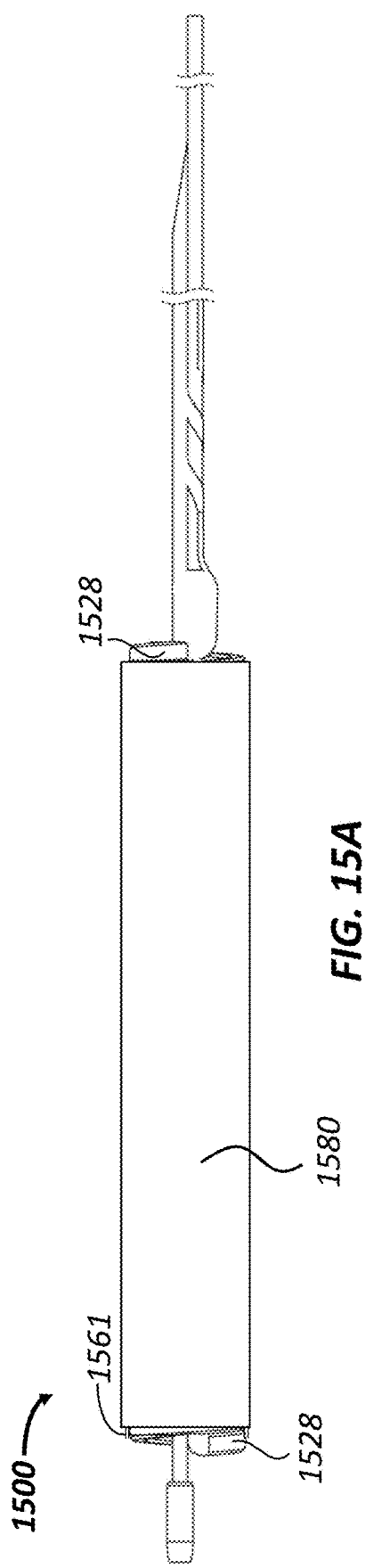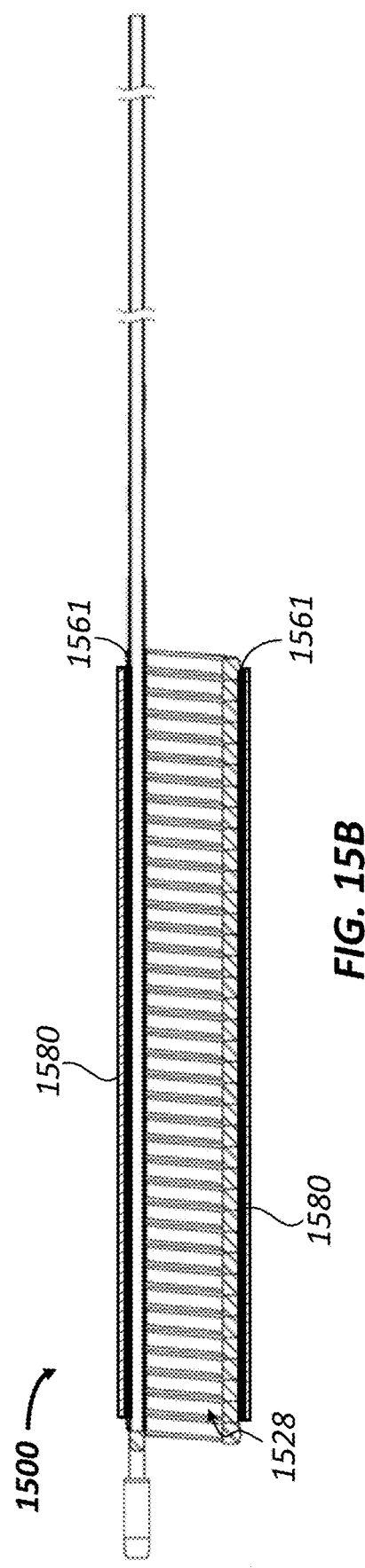

1700

1782
Passing a perfusion catheter, including a balloon, an elongate shaft that is attached to the balloon, and a containment structure surrounding at least a portion of the balloon, into a blood vessel until the balloon is positioned adjacent a lesion

1784
Inflating the balloon until an outer surface of the balloon contacts an inner surface of the blood vessel by urging fluid through a lumen of the elongate shaft and into the balloon

1786
The balloon, upon inflation, moving from a deflated configuration to an inflated configuration at which an outer surface of the containment structure engages the wall of the blood vessel

1788
Maintaining the balloon in the inflated configuration at the lesion during removal of the containment structure and release of a bioactive layer into the wall of the blood vessel.

*FIG. 17*

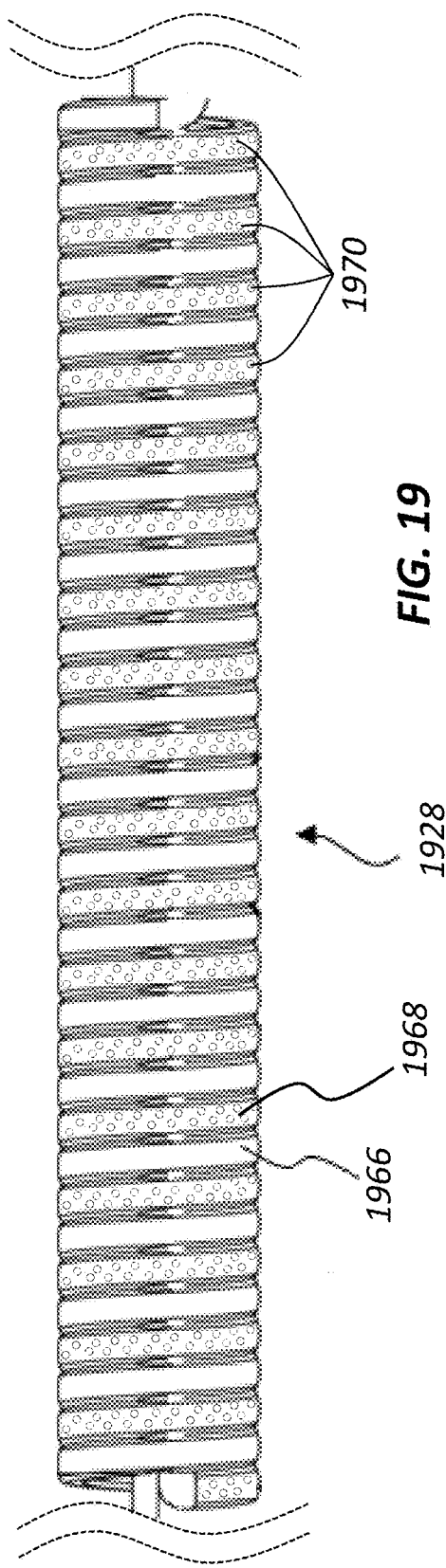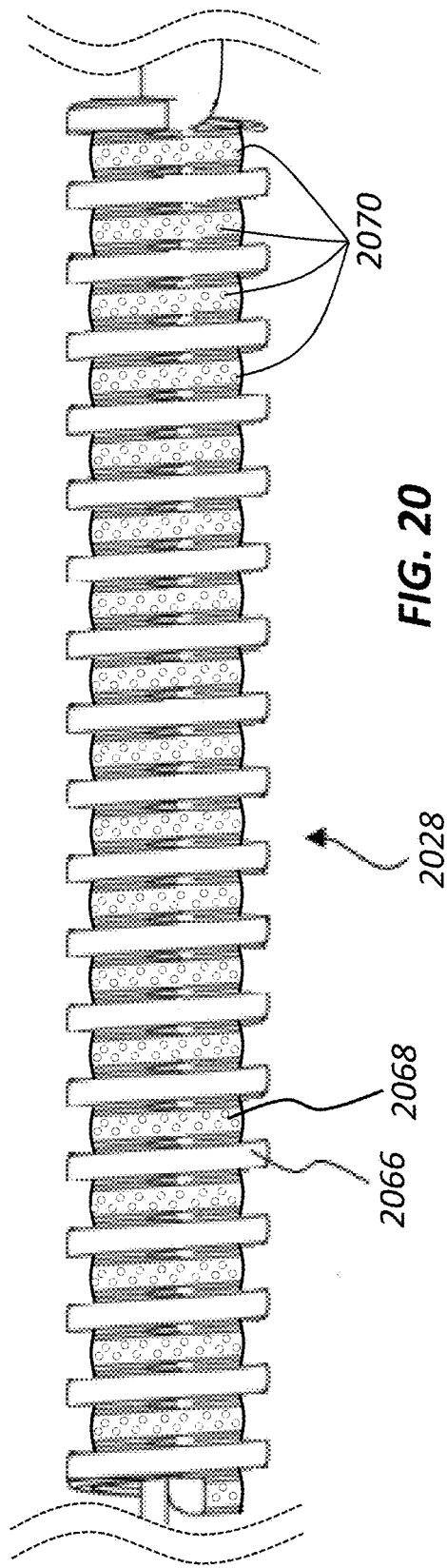

ELUTING PERFUSION CATHETERS AND RELATED METHODS

CLAIM OF PRIORITY

This non-provisional patent document claims the benefit of priority under 35 U.S.C. § 119(e) to U.S. provisional patent application bearing Ser. No. 62/719,000, entitled "ELUTING PERFUSION CATHETERS AND RELATED METHODS" and filed on Aug. 16, 2018, which is herein incorporated by reference in its entirety.

TECHNICAL FIELD

The subject matter of this patent document relates to the field of medical devices. More particularly, but not by way of limitation, the subject matter relates to catheters and related methods for treating a blood vessel.

BACKGROUND

Vascular lesions or other abnormalities result from a wide range of ailments, and may even be formed during treatment of such ailments. Partial or total occlusions can slow and even stop blood flow, and vascular tears can allow blood leakage.

A severe or chronic total occlusion (CTO) is a vessel blockage that prevents blood flow beyond the occlusion. Chronic total occlusions most often occur in coronary and peripheral arteries and result from atherosclerosis.

A procedure for treating CTOs and other blockages is percutaneous transluminal angioplasty.

During an angioplasty procedure, access to a desired blood vessel is obtained and a guidewire is introduced into the blood vessel. The guidewire can be maneuvered into place, including being passed into and through the occlusion, and acts as a guide for positioning a subsequent treatment device used to dilate or otherwise treat the vessel occlusion. The treatment device can be advanced over the guidewire so that its distal portion is positioned within the occlusion. A dilatation balloon at the distal portion of the treatment device can then be inflated to apply radial pressure to the occlusive material and adjacent inner wall portions of the vessel, thereby clearing or widening the occlusion to enable better blood flow.

Coated medical devices may be employed during an angioplasty procedure, or various vascular procedures, to apply a therapeutic drug directly to the treatment site. Such devices can include drug-eluting stents configured to release a drug after coming into contact with a tissue.

OVERVIEW

The present inventors recognize that various types of tissue damage and/or blockage at or within a blood vessel, including partial lesions, blockages and other abnormalities, present diverse challenges requiring an assortment of interventional treatment approaches. CTOs are one of the most challenging lesion subsets in interventional cardiology to treat due to their established occlusive structure. Complications related to CTO and partial occlusion interventions include recoil or rebuilding of a lesion and vessel wall perforation or dissection.

Conventional balloon catheters cause complete interruption of blood flow within the damaged vessel while the catheter's balloon is inflated. Keeping the balloon inflated for an extended period can risk damage to bodily regions nourished by the vessel-regions already weakened by insufficient blood supply. The present inventors recognize that most adults are only able to withstand non-perfusion dilation of 30-45 seconds without significant side effects.

The present inventors further recognize that drug-eluting devices often fail to retain or deliver a treatment-effective amount of drug to tissue at a targeted vessel site, for example due to immediate dissolving and loss of the drug on its way to the treatment site. Excessive dissolving may also occur as eluted drug is flushed (by flowing blood) from the targeted tissue between balloon inflation cycles. Short windows of vessel wall contact time at the treatment site may further limit the effectiveness of drug-eluting devices that require direct surface contact with a lesion. As a result, ineffective amounts of the drug may be applied at the treatment site, and substantial waste of expensive therapeutics incurred.

The present perfusion catheters (which can also be referred to as perfusion catheter assemblies) can be easily deployed, inflated, and deflated in a damaged vessel. The catheters also provide a passage (or flow lumen) formed upon inflation of its balloon, such that blood continues passing through the treatment site, which allows the balloon to remain inflated for longer periods of time as a treatment drug is eluted and received by the vessel wall. A perfusion catheter can include a balloon formed of an inflatable tube and an elongate shaft having a lumen for providing inflation fluid to, or withdrawing inflation fluid from, the balloon. In some embodiments, the inflatable tube can be coiled in a helical manner around a central axis into a series of windings. Adjacent windings can be stacked against and bonded to each other or laterally spaced, and an inner surface of the series of windings, when inflated, can define the passage. The perfusion catheter can include a bioactive layer, which may include one or more drugs and/or excipients to be released at a target site. The perfusion catheter may also include a containment structure on the balloon, where the containment structure is configured to retain the drugs/excipients until the balloon arrives at a treatment site within a damaged vessel. Examples may also exclude the bioactive layer or containment structure. For instance, a perfusion catheter may include a balloon comprised of an inflation filar and an elution filar interwoven in an alternating manner. The elution filar may include perforations or holes configured to release the drugs and/or excipients at the treatment site.

The present methods for treating vascular lesions or abnormalities of various types and delivering a bioactive substance can include inserting a guidewire into a blood vessel and advancing the guidewire to or across a treatment site, passing a perfusion catheter over the guidewire until a distal portion of the perfusion catheter is positioned near or within the treatment site, and inflating a balloon of the perfusion catheter. In some embodiments, inflating the balloon can include inflating a series of windings of helically-wound tubing, which may be contacting or laterally spaced. The balloon, upon inflation, can move from a deflated configuration to an inflation configuration at which an outer surface of the balloon can engage a wall of the blood vessel and an inner surface of the balloon can define a passage. The balloon may be covered in a bioactive layer, which includes at least one bioactive substance for targeted release at the treatment site. In some examples, the balloon may be surrounded by a containment structure configured to protect the bioactive layer from premature loss. The passage can allow a flow of bodily fluid, such as blood, through the perfusion catheter. Optionally, the method can include passing a treatment device at least partially through the passage. The balloon can remain inflated for an extended period of time, e.g., 60 seconds to 120 seconds or more, while a drug or other bioactive substance is eluted from the device. After treatment, the balloon can be deflated in a distal-to-proximal or proximal-to-distal direction and removed through the guide catheter.

These and other examples of the present perfusion catheters and related methods will be set forth in the following Detailed Description. This Overview is intended to provide non-limiting examples of the present subject matter—it is not intended to provide an exclusive or exhaustive explanation. The Detailed Description below is included to provide further information about the present perfusion catheters and related methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIG. 15A illustrates an enlarged side view of a distal portion of a drug-eluting perfusion catheter including a dedicated guidewire lumen and a containment structure, as constructed in accordance with at least one embodiment.

FIG. 15B illustrates a cross-sectional side view of the drug-eluting perfusion catheter shown in FIG. 15A.

FIG. 17 illustrates a method of using a present catheter to navigate through vasculature and apply a drug at a treatment site, as constructed in accordance with at least one embodiment.

FIG. 19 illustrates an enlarged side view of another inflated balloon included with a perfusion catheter, as constructed in accordance with at least one embodiment.

FIG. 20 illustrates an enlarged side view of another inflated balloon included with a perfusion catheter, as constructed in accordance with at least one embodiment.

Figure 1:
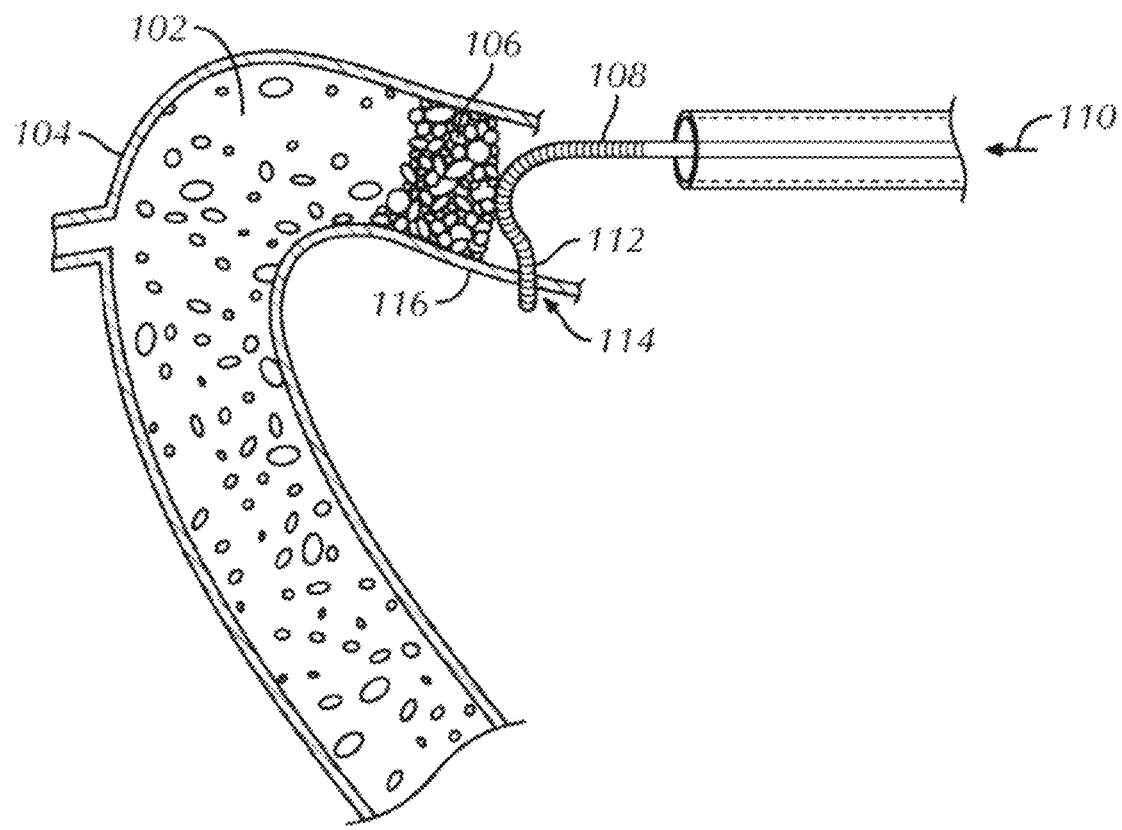
FIG. 1 illustrates a schematic view of a guidewire advanced through a patient's vasculature and unable to penetrate an end cap of an occlusion within a vessel.

The drawing figures are not necessarily to scale. Certain features and components may be shown exaggerated in scale or in schematic form and some details may not be shown in the interest of clarity and conciseness.

DETAILED DESCRIPTION

The present catheters and methods provide clinicians with a means to treat a range of vascular abnormalities, including vessel occlusions (e.g., CTOs and partial blockages) and/or complications (e.g., perforations and dissections) related to occlusive angioplasty interventions. The present catheters and methods also provide means to treat a vessel occlusion while maintaining a passage through the treated vessel segment. The present catheters and methods also provide the clinicians with a means to safely and effectively remove all interventional devices after treating a targeted tissue. While the catheters and methods are primarily discussed in relation to treatment of coronary arteries, they may also be useful in other blood vessels throughout the body including peripheral arteries and veins.

Figure 2:
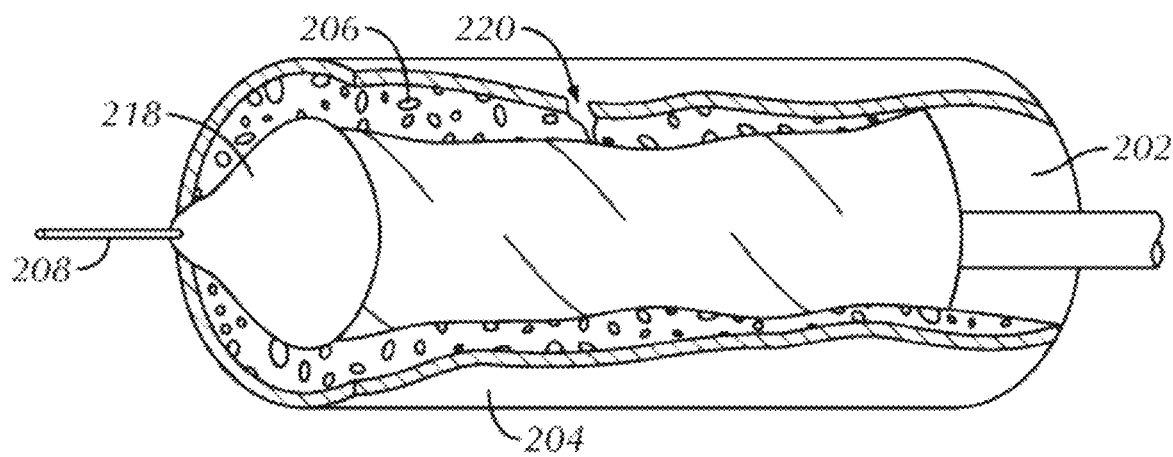
FIG. 2 illustrates a schematic view of a distal portion of a treatment device dilating an occlusion within a vessel segment, such dilation causing dissection of the vessel's wall.

FIGS. 1 and 2 provide examples of complications that may be related to CTO angioplasty interventions in which the present perfusion catheters and related methods can be beneficial. In patient's suffering from a CTO, successful treatment of the occlusion can be challenging. A factor that can determine whether a treating clinician can successfully treat the occlusion is the clinician's ability to advance a guidewire from a first side of the occlusion to a second side of the occlusion. In some instances, such as when the natural lumen 102 of a blood vessel 104 is totally occluded by hard plaque 106 (e.g., calcified atherosclerotic plaque), the guidewire 108 cannot cross the occlusion and, in response to a continued proximally-applied pushing force 110, its distal portion 112 may deviate to, and perforate 114, an adjacent vessel wall 116, as shown in FIG. 1.

In other instances, such as when the occlusive material 206 is soft or where the occlusion has a tiny opening, the guidewire 208 can bed forced through the occlusive material and allowed to remain within the natural lumen 202 of the blood vessel 204. A treatment device, such as a balloon catheter 218, can be guided over the guidewire 208 to the occlusion site where it can be used to carry out dilation treatment. Mechanical dilatation of the vessel 204 with the balloon catheter 218 can be associated with plaque fracture, intimal wall splitting, and localized medial dissection. Dissection 220, if it occurs, may propagate into the media and through the adventitia (the outermost layer of the vessel wall), resulting in another form of coronary perforation as shown in FIG. 2.

Perforations and dissections are serious complications for a catheterization laboratory because of their associated morbidity and mortality rates and, for this reason alone, their management and treatment is important and should be initiated quickly. A first step in management and treatment can be the placement of a balloon to seal the perforation or dissection. Prolonged balloon inflation may successfully seal the perforation or stop the propagation of the dissection and can provide time to prepare and implant a covered stent, if needed.

The present perfusion catheter 300 can be used in cases where there is a vessel perforation or dissection to be treated and further in cases where there is occlusive material, e.g., partial or total, to be dilated and treated with a substance formulated to prevent regrowth of the occlusion. The catheter 300 can also be used in cases where there is no perforation or dissection, but where treatment is otherwise needed. The catheter 300 can be advanced through a guide catheter and directed through vasculature for treatment of the vessel wall injury using a guidewire and optionally a placement catheter. The perfusion catheter 300 can include a proximal manifold 324 for coupling with an inflation syringe, an elongate shaft 326, and a distal balloon 328 to seal the perforation or dissection or dilate the occlusive material. In various embodiments, the perfusion catheter 300 (or any of the perfusion catheters disclosed herein) may be used as a dilatation device and a drug-delivery device, or as a drug-delivery device only. In some examples, any of the perfusion catheters disclosed herein, including perfusion catheter 300, may be used in conjunction with a separate dilatation device, e.g., a percutaneous transluminal coronary angioplasty (PTCA) device.

The elongate shaft 326 can serve two primary purposes. First, the elongate shaft 326 can transmit forces applied by a clinician to either advance or retract the perfusion catheter 300, and specifically the balloon 328, during an angioplasty or sealing procedure. By manipulating the elongate shaft 326, the balloon 328 can be inserted into and passed through a guide catheter and out the distal portion of the guide catheter to a perforation or dissection to be sealed or an occlusion to be dilated. Second, the elongate shaft 326 can optionally include a lumen 330 for providing inflation fluid to, or withdrawing inflation fluid from, the balloon 328. The lumen 330 of the elongate shaft 326 can be in fluid communication with the manifold 324, couplable to an inflation syringe, at its proximal portion 332, and it can be in fluid communication with the interior of the balloon 328 near its proximal or distal portion 334. Alternatively, a separate inflation structure spanning the distance between a manifold and the balloon 328 can be used.

The elongate shaft 326 can be eccentrically attached to a proximal or distal portion 336 of the balloon 328 and can extend proximally for clinician accessibility outside the guide catheter. The elongate shaft 326 can, for example, be attached to the balloon 328 by wrapping the balloon 328 about the shaft's intermediate 338 or distal 334 portions and affixing it thereto. In an example, the elongate shaft 326 is attached to the distal portion 336 of the balloon 328 for a minimum of 5 mm.

Figure 3:
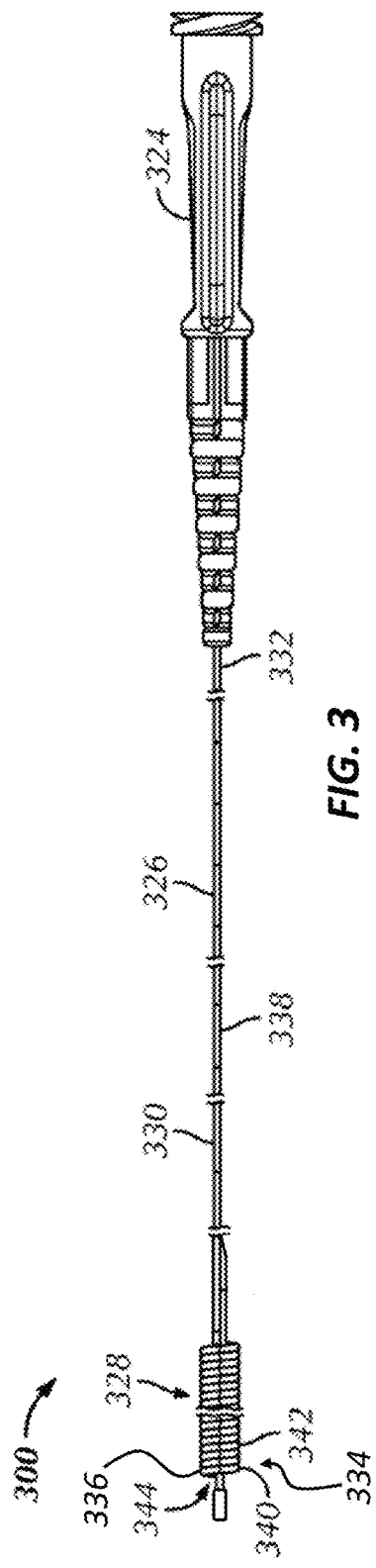
FIG. 3 illustrates a side view of a perfusion catheter, as constructed in accordance with at least one embodiment.

The embodiment of FIG. 3 illustrates that the balloon 328 can be formed from an inflatable tube 340 coiled in a helical or spiral manner around a central axis into a series of windings 342 (or loops), with consecutive or adjacent windings 342. The windings 342 may be stacked against and contacting each other with substantially no space therebetween, which can ensure the windings 342 act as a unit. Alternatively, the windings 342 may be spaced apart such that adjacent windings do not contact each other. Spaced windings 342 may be preferred for non-coronary applications, which may involve positioning the balloon 328 in veins of greater diameter. As further described herein, adjacent windings 342 may have the same or different diameter after inflation. The inner surfaces of the windings 342 can define a passage 344 through the open center of the helix when the coiled balloon 328 is inflated. The passage 344 can extend the full length of the balloon 328 to permit blood or other bodily fluid to perfuse (or flow) therethrough, which is important since cutting off blood supply for extended periods of time is undesirable. When the balloon 328 is deflated, it can collapse or flatten into a low profile configuration, which may comprise one or more folds that wrap around the distal portion 334 of the elongate shaft 326. An elastic sheath can optionally be disposed around the balloon 328 and be utilized to reduce the collapsed profile of the deflated balloon so that it can be more easily inserted or removed from a patient.

In some examples, the inflatable balloon may not include helical windings and/or may not define a passage 344. According to such examples, the inflatable balloon may include or be coupled with an internal shunt tube configured to maintain blood flow therethrough while the balloon is inflated. The specific configuration of the perfusion catheter thus may vary, and is not limited to the helically-wound balloon examples disclosed herein for illustration. In some examples, the inflatable balloon may even be used in conjunction with a separate dilatation device.

Because the passage 344 is created by the balloon 328 in the example shown, blood flow is permitted through the passage 344 and the overall perfusion catheter 300 can be kept to a minimal size. This physical attribute allows the catheter 300 to be of a small diameter when it is inserted into the patient's body and maneuvered to the desired position, yet provides a relatively large blood flow passage when the balloon 328 is inflated.

Figure 4:
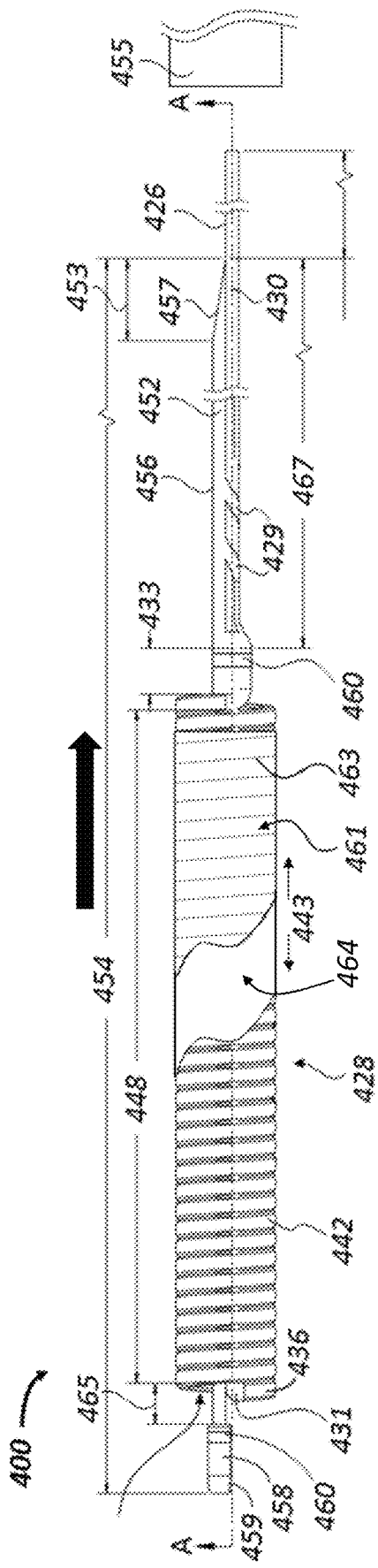
FIG. 4 illustrates an enlarged side view of a distal portion of a perfusion catheter including a dedicated guidewire lumen, as constructed in accordance with at least one embodiment.

FIG. 4 illustrates an enlarged side view of a distal portion of a perfusion catheter 400, as constructed in accordance with at least one embodiment. The catheter 400 can be provided with a guidewire lumen 452 separate from a passage 444 defined by windings 442 of a balloon 428 and separate from a lumen 430 of an elongate shaft 426 for providing inflation fluid to, or withdrawing inflation fluid from, the balloon 428. In the example shown, the windings 442 are stacked against each other, but in additional embodiments, the windings can be spread apart, such that a lateral space 443 is defined between them. The guidewire lumen 452 can have a length 454 approximately equal to, or slightly longer than, the length 448 of the passage 444 and can be positioned therein. An outer surface of a guidewire support tube 456 forming the guidewire lumen 452 can contact inner surfaces of the windings 442 of the balloon 428 and can optionally be inset in these inner surfaces. Polymers of the guidewire support tube 456 and the balloon 428 can be configured to adhere to each other upon application of heat treatment. A proximal end 457 of the guidewire support tube 456 may define a skived entry configured to receive the guidewire in some examples. In various examples, the proximal end 457 may define a length 453 ranging between 2 mm and 5 mm, inclusive. In some embodiments, the elongate shaft 426 and the proximal end 429 of the balloon 428 may be fused together along a distance 467 of the guidewire lumen 452.

A distal end 436 of the balloon 428 can be fluidly coupled with a distal end 431 of the lumen 430 of the elongate shaft 426, such that inflation fluid is added and removed at the distal end 436 of the balloon. The balloon 428 can be helically coiled proximally from its distal end 436, and a proximal end 429 of the balloon 428 may comprise a tail portion wrapped around the inflation lumen 430, thereby sealing the proximal end 429. Proximal wrapping of the balloon 428 may be implemented without heat shrinking or adhesive application in various implementations. Because the proximal end 429 of the balloon 428 can be sealed and inflation fluid can only be removed via its distal end 436, deflation of the balloon 428 may occur in a distal-to-proximal direction, in the direction of the arrow toward a guide catheter 455. Accordingly, when the catheter 400 is deflated and pulled proximally back into a guide catheter, the inflation fluid may not become trapped or sequestered in any portion of the balloon 428. This facilitates effective and safe removal of the catheter 400 from a treatment site, for example by decreasing the cross-sectional diameter of the deflated balloon, which may occur approximately simultaneously with deflation. Complete deflation may also reduce the risk of puncturing or tearing the balloon 428 upon its reentry into the guide catheter 455. In examples, a maximum distance 433 of about 2 mm of the balloon may not be reflowed.

The guidewire lumen 452 can be designed to receive and facilitate tracking of a previously positioned guidewire having its distal portion in position near or across a treatment site. The perfusion catheter 400, and specifically the guidewire support tube 456, can be slid over the guidewire and advanced to the treatment site. An inner diameter of the guidewire support tube 456 can be sized to be advanced over a 0.36 mm (0.014 in) guidewire, for example. An atraumatic distal end portion 458 culminating in a tapered tip 459 can be disposed at a distal tip of the guidewire support tube 456 to prevent the perfusion catheter 400 from perforating a blood vessel during deployment and use. In various examples, a proximal portion of the distal end portion 458 can be distally offset by a distance 465 ranging from about 0.1 mm-5 mm. Since the guidewire support tube 456 can be short compared to the total lengths of the catheter 400 and the guidewire, the use of the guidewire support tube 456 as a guide permits rapid exchange of the catheter 400 over the guidewire.

One or more radiopaque markers 460 can be placed on the guidewire support tube 456 or the elongate shaft 426 proximal or distal to the balloon 428. These markers 460 can facilitate proper placement of the balloon 428 relative to a vessel wall injury prior to its inflation and can be any suitable radiopaque material detectable through the use of x-ray or fluoroscopy. Materials such as the platinum series of metals (e.g., platinum or palladium), gold, silver, iridium, or tantalum can be used as the markers. Certain stainless steels can also be suitable for use as markers. Alternatively, the polymer used in portions of the perfusion catheter 400 can be radiopaque or made so by addition of filler such as barium sulfate, bismuth trioxide, bismuth carbonate, tungsten, tantalum, or the like.

As further shown in FIG. 4, the catheter 400 can include a bioactive material coating or layer 461 ("bioactive layer") covering all or a portion of the inflatable balloon 428. The bioactive layer 461 can be relatively thin, such that ridges 463 from the underlying balloon 428 are visible at the outer surface of the layer 461. In various examples, the bioactive layer 461 can conform with the outer surface of the balloon 428. In addition or alternatively, the bioactive layer 461 can fill the spaces between the helical windings comprising the balloon 428, thereby creating a substantially uniform, even external surface.

In some embodiments, the bioactive layer 461 can include or be overlaid upon a base layer 464 configured to fill the valleys or ridges 463 between adjacent windings of the balloon 428. The base layer 464, or coating, can be added to the exterior surface of the windings 442 of the balloon 428 prior to application of the bioactive layer 461, thereby providing a substantially even, smooth foundation to facilitate uniform application of the bioactive layer 461. In some examples, the base layer 464 can include one or more excipients. The excipient(s), hydrated by blood within a vessel after insertion, can serve as a wicking agent to enhance the release of bioactive layer 461 components, e.g., drugs, at a target site. The base layer 464 may also exclude excipients in some examples.

Applying the base layer 464 to an exterior surface of the windings 442 of the balloon 428 can involve dripping the components of the base layer, in liquid form, directly onto the external surface of the balloon 428, for example using a pipette. After drip-application, the base layer 464 may be allowed to air-dry. This application method, which may be referred to as the "pipette-drip coating method," may add less weight to the balloon 428 relative to a spray coating technique, for example, and may embody a more efficient use of the bioactive layer component(s). In some examples, application of the base layer 464 may be achieved via a dip-coating technique, which may generally involve dipping the balloon 428, for example in a semi-inflated state, into a liquid sample of base layer 464 components. After application of the base layer 464, via drip-coating, dip coating or otherwise, the ridges 463 may disappear or at least comprise a reduced depth. Other suitable methods may be used to apply the base layer 464.

Figure 16:
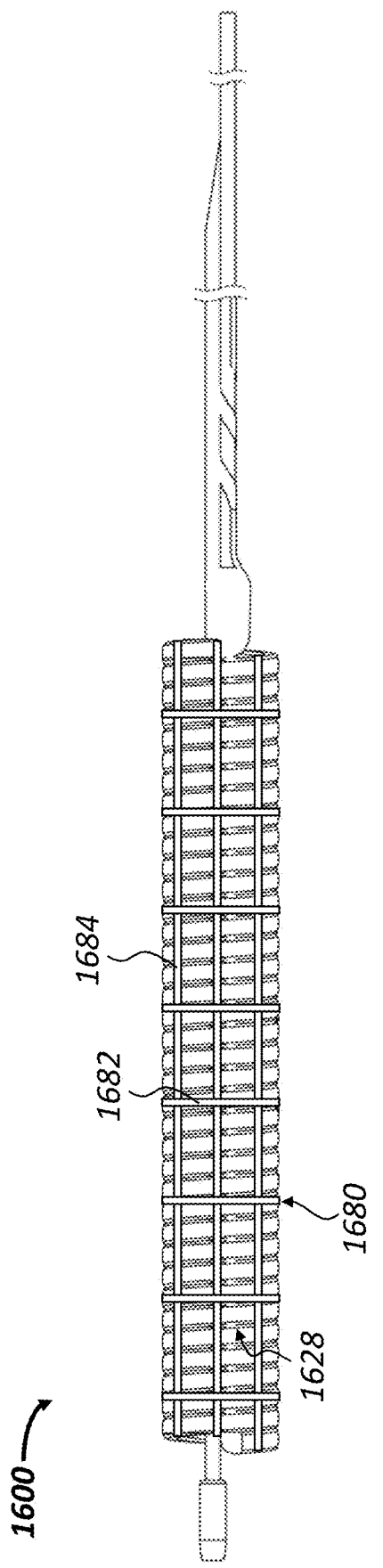
FIG. 16 illustrates an enlarged side view of a distal portion of another drug-eluting perfusion catheter including a dedicated guidewire lumen and a containment structure, as constructed in accordance with at least one embodiment.
Figure 21:
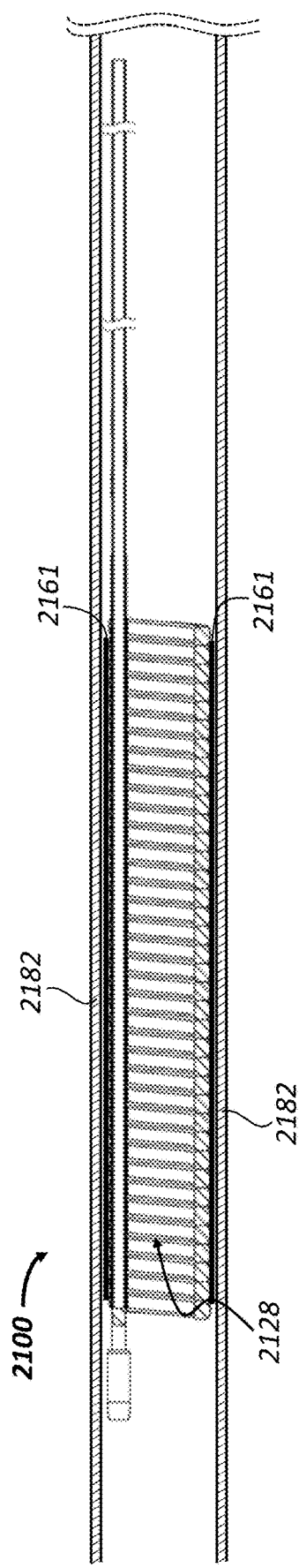
FIG. 21 illustrates an enlarged side view of a perfusion catheter coupled with a protective sheath, as constructed in accordance with at least one embodiment.

Within a blood vessel at a treatment site, e.g., total or partial occlusion site or site of vessel damage, the bioactive layer 461 may dissolve, break down or otherwise dissociate, thereby releasing one or more substances constituting the layer 461. The bioactive layer 461 may comprise one or more substances configured to treat the tissue at or near the treatment site. In various examples, materials constituting the bioactive layer 461 can include one or more drugs, therapeutic agents, diagnostic agents and additional or alternative substances having biological or pharmacological activity within a patient. Accordingly, the catheters disclosed herein can treat a wide range of ailments encompassing physical damage, e.g., vessel tearing, or other abnormalities treatable by one or more therapeutic substances. In various examples, the bioactive layer 461 may include one or more non-biologically derived substances and/or one or more substances not configured to treat the targeted tissue, i.e., biopassive substances. As shown in FIGS. 15, 16 and 21, the bioactive layer 461 may be covered by, or incorporated within, a containment structure or sheath. In some embodiments, the bioactive layer 461 and containment structure may comprise one integrally-formed component surrounding the inflatable balloon 428.

In specific embodiments, the bioactive material included in the bioactive layer 461 can include materials which prevent or slow restenosis and/or vessel closure. Such materials can include various thrombolytics, e.g., urokinase, streptokinase and/or tissue plasminogen activators, and/or various antithrombogenics, e.g., heparin, hirudin and/or antiplatelets, and/or various anti-inflammatory agents or steroids, e.g., dexamethasone, or combinations thereof. Antiproliferative agents, e.g., methotrexate, and/or chemotherapeutics, e.g., Paclitaxel, can also be included in embodiments of the bioactive layer 461. Additional examples of the wide range of substances that can be applied to the catheter 400 for targeted delivery include but are not limited to: one or more limus-based drugs, e.g., zotarolimus or sirolimus (rapamycin); estrogen or estrogen derivatives; thrombin inhibitors, hirulog, argatroban, D-phenylalanyl-L-poly-L-arginyl chloromethylketone; tissue plasminogen activators; fibrinolytic agents; vasospasm inhibitors; calcium channel blockers; nitrates, nitric oxide, nitric oxide promoters or other vasodilators; antimicrobial agents or antibiotics; aspirin, ticlopdine or other antiplatelet agents; colchicine or other antimitotics; microtubule inhibitors; cytochalasin or other actin inhibitors; remodelling inhibitors; deoxyribonucleic acid, an antisense nucleotide or another agent for molecular genetic intervention, GP IIb/IIIa, GP Ib-IX or another inhibitor or surface glycoprotein receptor; methotrexate or other antimetabolites or antiproliferative agents; dexamethasone, dexamethasone sodium phosphate, dexamethasone acetate, immunosuppressive agents; radiotherapeutic agents; iodine-containing compounds; barium-containing compounds; gold, tantalum, platinum, tungsten or another heavy metal functioning as a radiopaque agent; a peptide, a protein, an enzyme, an extracellular matrix component, a cellular component or another biologic agent, captopril, enalapril or another angiotensin converting enzyme (ACE) inhibitor, ascorbic acid, alphatocopherol, super-oxide dismutase, deferoxyamine, a 21-aminosteroid (lasaroid) or another free radical scavenger, iron chelator or antioxidant; angiopeptin; a 14C-3H-, 131I-, 32P or 36S-radiolabelled form or other radiolabeled form of any of the foregoing; or a mixture of any of the aforementioned substances.

In addition to a drug, the bioactive layer 461 can include one or more solvents, additives, adjuvants and/or excipients. Specific embodiments of the bioactive layer 461 can include at least one drug paired with at least one excipient. The excipient can be device- and/or drug-specific and can be formulated to improve drug transfer. For example, the excipient may prevent or at least decrease premature loss of the drug from the bioactive layer 461 and/or increase the speed and/or effectiveness of drug elution to the surrounding vascular tissue. The excipient, upon hydration, may facilitate transfer of the drug in its solid state, which may lead to more sustained drug activity. The excipient(s) can also improve the homogeneity of the bioactive layer 461, and may reduce agglomeration of the materials comprising the layer 461 upon insertion of the catheter 400 into a guide catheter. Example excipients may include, but are not limited to, one or more antioxidants, urea, dextrane, iopromide, shellac, butyryl-tri-hexyl citrate, citrate ester, SAFEPAX, shelloic acid, organic ester, propyl gallate and/or hydrophilic additives or enhancers, and combinations thereof.

The bioactive layer 461 can be added to the exterior surface of the balloon 428 according to various application techniques. In some examples, the bioactive layer 461 can be sprayed as a solution onto the balloon 428. In addition or alternatively, the bioactive layer 461 can be dipped or soaked in a solution of the bioactive material constituting the layer. Pursuant to both approaches, the balloon 428 may be dried, e.g., in a drying apparatus or by air-drying, after the solution of bioactive material is applied. In some embodiments, the balloon 428 can be coated with a matrix of bioactive material in a deflated or semi-inflated state. After application of the bioactive materials, the balloon 428 can be coiled or wrapped in a desired helical configuration in some embodiments. In alternative embodiments, a balloon can be filled with a bioactive inflation agent, which can be released at a target site through apertures defined by the balloon.

The amount of bioactive material applied to the balloon 428 may also vary, depending for example on dosage requirements, the type of material applied, the type of occlusion or lesion being treated, characteristics of the patient, etc. In various non-limiting examples, about 5 µg to about 1000 µg, about 10 µg to about 500 µg, or about 100 µg to about 200 µg of a drug may be included in the bioactive layer 461. Excipient doses may be lesser than, equal to, or greater than the drug doses.

As mentioned, the bioactive materials of the bioactive layer 461 can be applied as a solution. Solutions applied herein can include ethanol, isopropanol, ethyl acetate, diethyl ether, acetone, acetone, dimethyl sulfoxide, dimethyl formamide, glycerin, water or mixtures thereof.

Figure 5:
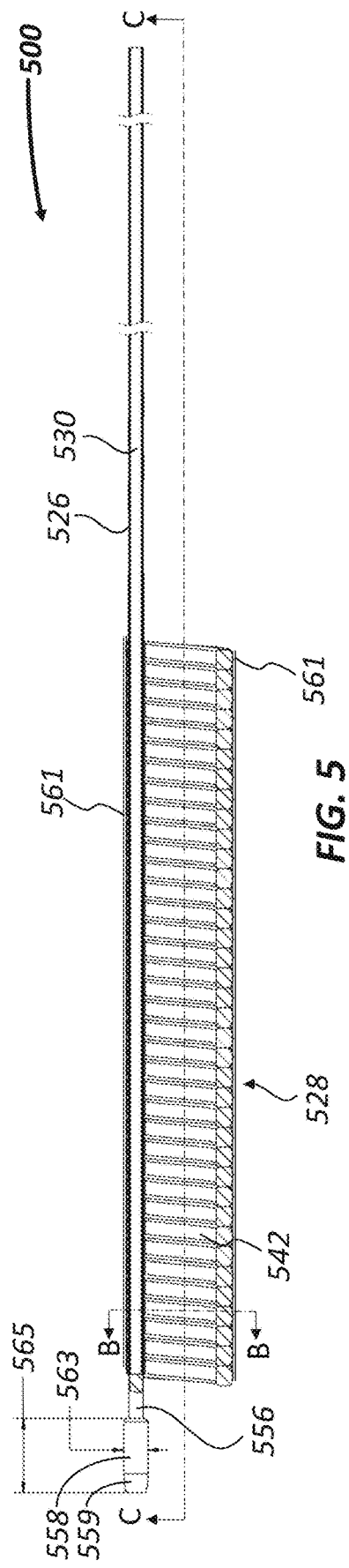
FIG. 5 illustrates an enlarged cross-sectional view of a distal portion of the perfusion catheter taken along line A-A of FIG. 4.

FIG. 5 illustrates a cross-sectional view of a catheter 500 (taken along line A-A of FIG. 4). As shown, the inflation lumen 530 of the elongate shaft 526 can longitudinally span the length of the balloon 528, such that each of the plurality of windings 542 cover the elongate shaft 526, which can be inset in the windings 542. The bioactive layer 561 is visible on the outermost edges of the balloon 428. The guidewire support tube 556 can extend for a distance beyond the distal end of the elongate shaft. In the embodiment shown, the distal end portion 558 of the guidewire support tube 556, including the tapered tip 559, can define a length 565 of about 3 mm. The length 565 may vary in examples, ranging from about 1 mm to about 6 mm, about 2 mm to about 5 mm, or about 1.5 mm to about 4.5 mm. The width 563 of the distal end portion 558 may also vary. In various embodiments, the maximum width of the distal end portion may be about 0.038 in. The minimum width may be adjustable, provided the width is sufficient to accommodate a guidewire for various applications. In examples, the width 563 may range from about 0.01 in to about 0.05 in.

Figure 6:
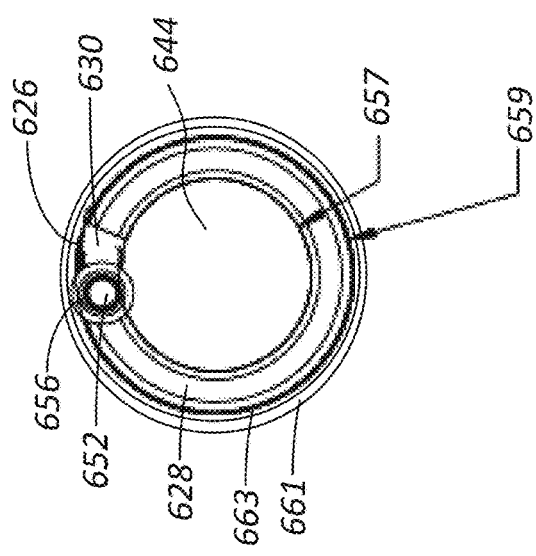
FIG. 6 illustrates an enlarged cross-sectional view taken along line B-B of FIG. 5.

FIG. 6 illustrates a cross-sectional view of an inflated balloon 628 and a guidewire support tube 656 and elongate shaft 626 extending therethrough, taken along line B-B of FIG. 5. The guidewire support tube 656 and the elongate shaft 626 can be embedded within a radial portion of the inflatable tube comprising the balloon 628, leaving the internal passage 644 unobstructed upon inflation of the balloon 628. In examples, the balloon windings can be bonded directly to the guidewire support tube 656 for the full length of the balloon, such that the guidewire lumen 652 and inflation lumen 630 are fully enveloped by the balloon 628. The cross-sectional widths of the bioactive layer 661 and optional base layer 663 are also shown.

The inner diameter 657 of the inflated balloon 628 can accommodate passage of various treatment devices, e.g., stents, therethrough. The inner diameter 657 may be about 3 mm in some examples, and can range in additional implementations from about 1 mm to about 6 mm, about 2 mm to about 5 mm, or about 1.5 mm to about 4.5 mm. The outer diameter 659 can also vary, depending for example on the diameter of a vessel at the targeted treatment site. In various embodiments, the outer diameter 659 can range from about 2 mm to about 8 mm, about 3 mm to about 6 mm, about 3.5 mm to about 5 mm, about 3.75 mm to about 4.25 mm, or about 4 mm.

Figure 7:
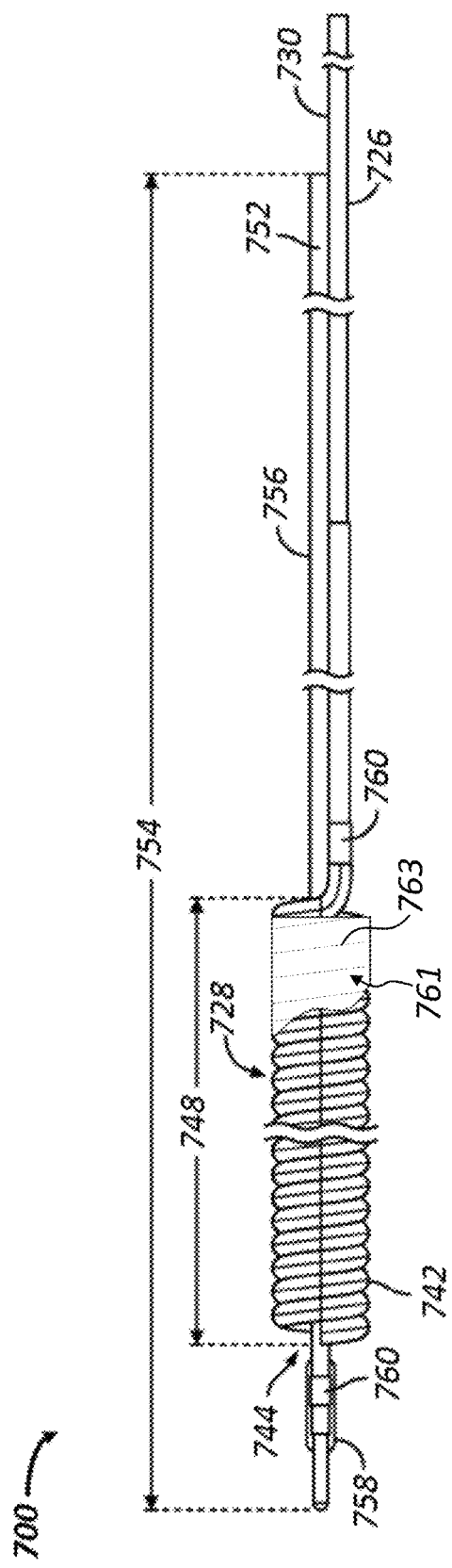
FIG. 7 illustrates an enlarged side view of a distal portion of a perfusion catheter, as constructed in accordance with at least one embodiment.

FIG. 7 illustrates an enlarged side view of a distal portion of another perfusion catheter 700, as constructed in accordance with at least one embodiment. Unlike the catheter 400 shown in FIG. 4, the catheter 700 may include a balloon 728 configured to inflate and deflate in a proximal-to-distal direction. The catheter 700 can be provided with a guidewire lumen 752 separate from a passage 744 defined by windings 742 of a balloon 728 and separate from a lumen 730 of an elongate shaft 726 for providing inflation fluid to, or withdrawing inflation fluid from, the balloon 728. The guidewire lumen 752 can have a length 754 approximately equal to, or slightly longer than, the length 748 of the passage 744 and can be positioned therein. An outer surface of a guidewire support tube 756 forming the guidewire lumen 752 can contact inner surfaces of the windings 742 of the balloon 728 and can optionally be inset in these inner surfaces. Polymers of the guidewire support tube 756 and the balloon 728 can be configured to adhere to each other upon application of heat treatment.

The guidewire lumen 752 is designed to receive and facilitate tracking of a previously positioned guidewire having its distal portion in position near or across a treatment site. The perfusion catheter 700, and specifically the guidewire support tube 756, can be slid over the guidewire and advanced to the treatment site. An inner diameter of the guidewire support tube 756 can be sized to be advanced over a 0.36 mm (0.014 in) guidewire, for example. An atraumatic tip 758 can be disposed at a distal tip of the guidewire support tube 756 to prevent the perfusion catheter 700 from perforating a blood vessel during deployment and use. Since the guidewire support tube 756 can be short compared to the total lengths of the catheter 700 and the guidewire, the use of the guidewire support tube 756 as a guide permits rapid exchange of the catheter 700 over the guidewire. One or more radiopaque markers 760 can be placed on the guidewire support tube 756 or the elongate shaft 726 proximal or distal to the balloon 728. These markers 760 can facilitate proper placement of the balloon 728 relative to a vessel wall injury prior to its inflation and can be any suitable radiopaque material detectable through the use of x-ray or fluoroscopy. Materials such as the platinum series of metals (e.g., platinum or palladium), gold, silver, iridium, or tantalum can be used as the markers. Certain stainless steels can also be suitable for use as markers. Alternatively, the polymer used in portions of the perfusion catheter 700 can be radiopaque or made so by addition of filler such as barium sulfate, bismuth trioxide, bismuth carbonate, tungsten, tantalum, or the like.

As further shown in FIG. 7, the catheter 700 can include a bioactive material coating or layer 761 ("bioactive layer") covering all or a portion of the inflatable balloon 728. The bioactive layer 761 can be relatively thin, such that ridges 763 from the underlying balloon 728 are visible at the outer surface of the layer 761. In some examples, the bioactive layer 761 can form a smooth, substantially even outer surface. The composition and configuration of bioactive layer 761 can be similar or identical to that of bioactive layer 461. Like perfusion catheter 400, the perfusion catheter 700 may also include a base layer underlying the bioactive layer 761 to fill the ridges between successive windings of the balloon 728. As shown in FIGS. 15, 16 and 21, the bioactive layer 761 may be covered by, incorporated within, or coupled to a containment structure or sheath configured to protect the bioactive layer within a vessel.

Figure 8:
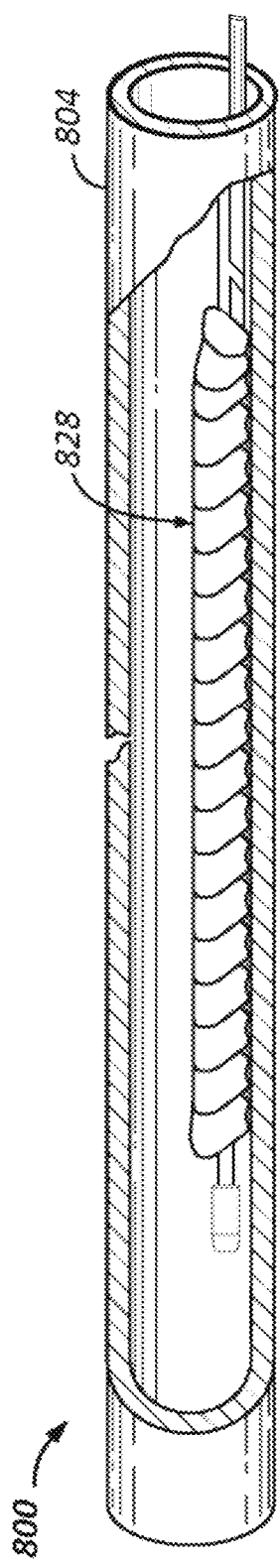
FIG. 8 illustrates an enlarged side view of a distal portion of a perfusion catheter with its balloon in a deflated configuration within a vessel segment.

FIG. 8 illustrates a perfusion catheter 800 in a blood vessel 804 of a patient. The catheter 800, and specifically a balloon 828 of the catheter, can be introduced and advanced within the blood vessel 804 in a low profile, unexpanded configuration. In this configuration, the balloon 828 is in a relaxed, folded, or crushed configuration and does not significantly increase the overall diameter of a distal portion of the catheter 800 such that it can be inserted into the patient and guided through the patient's vasculature to the desired treatment site. As described further in connection with FIGS. 15, 16 and 21, the balloon 828 of the catheter 800 may be contained within an outer containment structure or sheath configured to protect the bioactive layer on the balloon 828 from dissolving or otherwise breaking down before inflation of the balloon at the treatment site.

Figure 9:
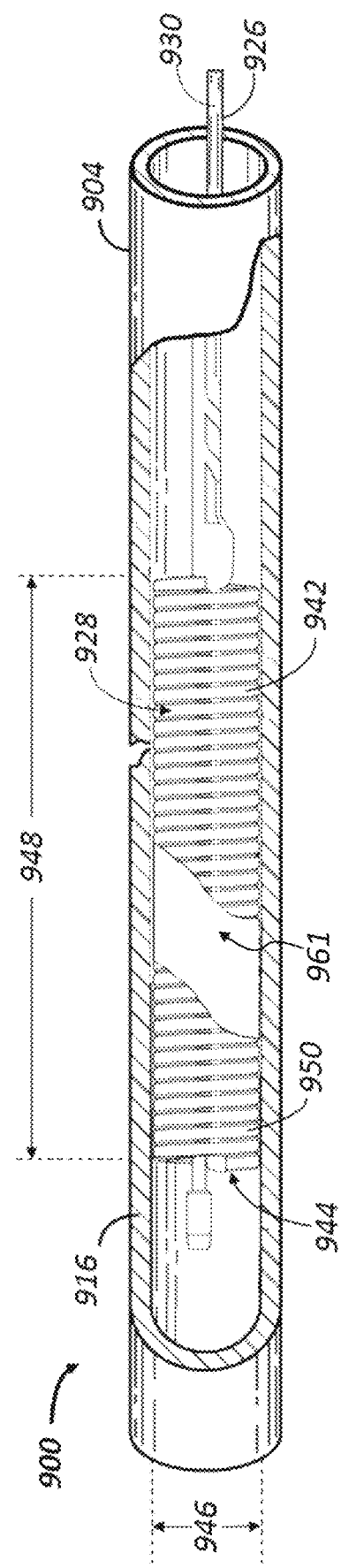
FIG. 9 illustrates an enlarged side view of a distal portion of the perfusion catheter with its balloon in an inflated configuration within a vessel segment.

Once at the treatment site, the balloon 928 can be inflated as illustrated in FIG. 9. Fluid under pressure can be supplied to the balloon 928 through an inflation lumen 930 of an elongate shaft 926, thereby expanding the balloon 928 toward a wall 916 of the blood vessel 904, such as for sealing, opening, or otherwise treating it. When inflated, the bioactive layer 961 of the balloon 928 can impinge upon or engage the vessel wall 916 at the treatment site at pressures of 2 atm-20 atm, for example, yet blood can be allowed to flow through the passage 944 defined by the balloon's windings 942. In some examples, blood can be allowed to flow through a tube passing through the balloon, for example in embodiments of the balloon that do not include helical windings defining a central passage. In some examples, the bioactive layer 961 may be contained within an outer containment structure or sheath, such that the containment structure or sheath may initially impinge against an inner surface of the vessel wall 916, at least for a period prior to the structure being dissolved or removed. The structure can be flexible to accommodate inflation of the balloon 928 without constriction thereof. Since the passage 944 created through the windings 942 is relatively large compared to the size of the vessel 904, the interruption of blood flow through the vessel is minimized and the perfusion catheter 900 is capable of prolonged inflation for temporary hemostasis in coronary perforations or dissections. In some embodiments, the balloon 928 may remain inflated for between 60 and 180 seconds, or for at least 60 or 120 seconds. In some examples, acceptable inflation times may extend for 2 or more minutes, e.g., 5, 10, 15 or more minutes. During this time, the bioactive materials comprising the bioactive layer 961 may be released into the surrounding wall 916. By increasing the length of time that the balloon is inflated and the bioactive materials released, the catheter 900 may increase the effectiveness of treatment elicited by the materials of the bioactive layer, for example by delivering greater amounts of the materials to the treatment site. While the bioactive layer 961 of FIG. 9 only covers a portion of the balloon 928, it should be understood that the bioactive layer 961 may span all, or at least half of, the length of the inflated balloon 928.

Beyond allowing for fluid flow, the passage 944 of the balloon 928 can be adapted to slidably receive a treatment device (e.g., a smaller diameter balloon catheter, stent catheter, guidewire support catheter, or guidewire). The balloon 928 can include any number of windings 942 in a number of sizes and configurations depending upon the particular treatment site, procedure and/or patient. Increasing the number of windings 942 in the balloon 928 can increase the ability of the balloon 928 to maintain a dilated state of an occlusion. The passage 944 can have a diameter 946 ranging from 2 mm-6 mm and can extend 10 mm-50 mm in length 948, for example. In additional examples, the passage 944 can be longer, ranging from 50 mm to 150 mm, for instance. The diameter 946 of the passage 944 can be sufficiently large to permit entry of a stent catheter. The present inventors recognize that plaque has a tendency to return to its original form and restrict passage. This restenosis, if it occurs, can occur as quickly as a few minutes. The perfusion catheter

900 allows the stent catheter to be delivered through the catheter while the balloon 928 dilates the occlusion. In this way, there can be minimal time between occlusion dilation and placement of a stent. The diameter 946 of the passage 944 can be sufficiently large to receive a guidewire support catheter to help pre-dilate or otherwise establish a pilot opening through the occlusion, or to receive the distal portion of a retrograde guidewire that is funneled into the passage 944 as a result of engagement between an outer surface 950 of the balloon 928 and the vessel wall 916.

When the procedure is completed, the balloon 928 can be deflated by applying vacuum to a proximal manifold coupled with the inflation lumen 930 of the elongate shaft 926. The entire perfusion catheter 900 can then be removed.

Figure 10:
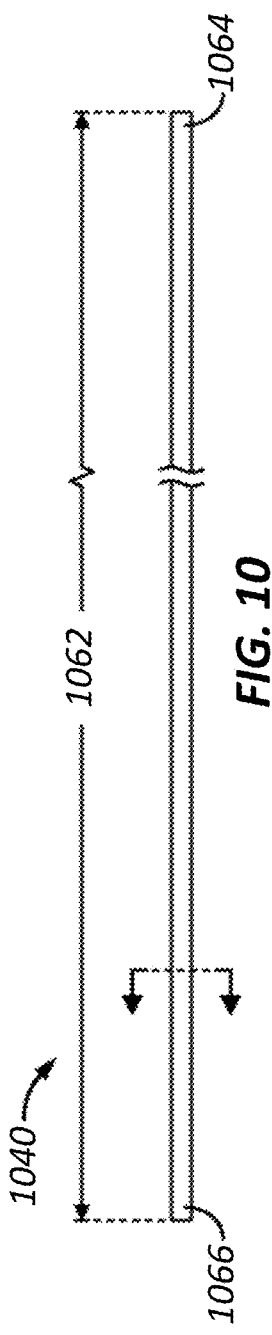
FIG. 10 illustrates extruded tubing of a perfusion catheter, as constructed in accordance with at least one embodiment.
Figure 11:
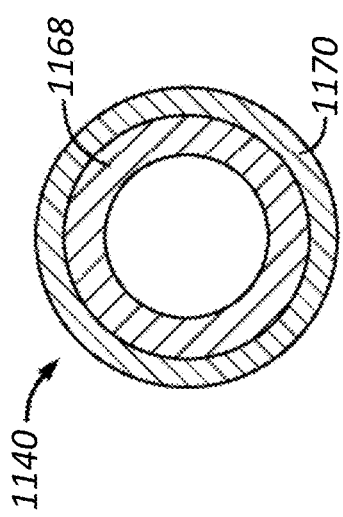
FIG. 11 illustrates a cross-sectional view of the extruded tubing shown in FIG. 10.

FIGS. 10 and 11 respectively illustrate side and cross-sectional views of extruded tubing 1040 for use in a balloon of a perfusion catheter, as constructed in accordance with at least one embodiment. The extruded tubing 1040 can have a uniform outer diameter along its length 1062 or can have a larger diameter along a majority of its length and tapered down on its proximal 1064 and distal 1066 portions. The distal portion 1066 of the extruded tubing 1040 can be closed by crimping the tubing and/or plugging it with a thermoplastic filler or the like. The length 1062 of the extruded tubing 1040 can range from 40 cm-120 cm before being coiled in a helical or spiral manner into a series of windings.

The coiled shape of the balloon can be maintained by causing adjacent windings to adhere to one another and the integrity of the balloon can be internally provided within each winding. These qualities can be accomplished by coextruding a combination of nested polymers which, after winding of the coil, can be heat treated to allow adjacent coils to stick to each other. In the example of FIG. 11, the extruded tubing 1140 is formed by coextruding two different polymer tubes 1168, 1170 (or layers), one slightly smaller than the other. The coextrusion process can eliminate seams, which are found in existing balloon designs, form tight bonds, and create a balloon using a reduced number of manufacturing steps. Alternatively, the smaller tube 1168 can be inserted inside the larger tube 1170 post-extrusion.

The smaller, inner tube 1168 can be formed from a polymer having sufficient radial stiffness to resist collapse or bursting when exposed to inflation pressures, and the larger, outer tube 1170 can be formed from a polymer configured to exhibit adhesive properties when heated and compliant properties when used within the body. The adhesive properties of the outer tube 1170 can allow adjacent windings to adhere to one another. The use of a compliant material for the outer tube 1170 can enable the balloon to conform to a vessel wall at the site of a perforation or tear, so that a substantial portion of the balloon's outer surface can be compressed against the vessel wall, or at the site of an occlusion that can benefit from being dilated. In various examples, the inner tube 1168 can include polyethylene terephthalate (PET) or Pebax® polyether block amides (which are available from Arkema) having an outer diameter of 0.2 mm-0.28 mm and an inner diameter of 0.12 mm-0.18 mm, and the outer tube 1170 can include Hytrel® polyester elastomer (which is available from E.I. du Pont de Nemours and Company), Pebax, or nylon having an outer diameter of 0.28 mm-0.36 mm and an inner diameter of 0.20 mm-0.28 mm. The inner 1168 and outer 1170 tubes can include polymers having different melting or softening temperatures, with the inner tube 1168 including the polymer with the higher melting temperature. The inner 1168 and outer 1170 tubes can include the same or similar polymers, with the polymer of the inner tube 1168 being cross-linked for strength and with the polymer of the outer tube 1170 not being cross-linked.

Figure 12:
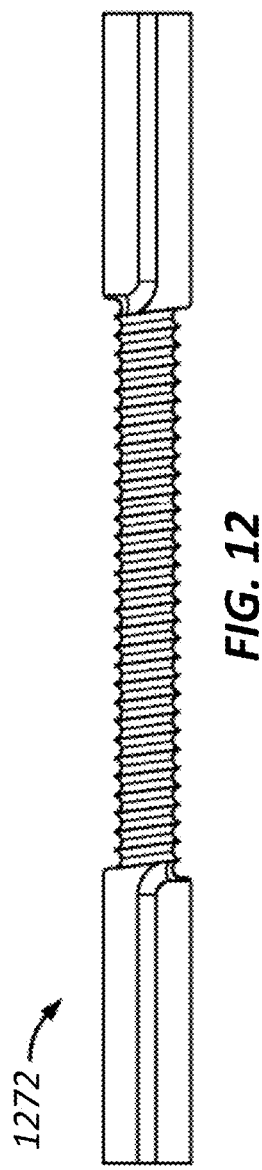
FIG. 12 illustrates a mandrel for manufacturing a balloon of a perfusion catheter, as constructed in accordance with at least one embodiment.

FIG. 12 illustrates a mandrel 1272 for coiling extruded tubing in a helical manner around a central axis into a series of windings to form a balloon. The extruded tubing can be wrapped in a proximal or distal direction about the mandrel 1272, which includes a shape of the intended profile of the balloon. After being wrapped onto the mandrel 1272, the extruded tubing can be pressurized or inflated and adjacent windings can be heat set in order to ensure that they adhere to one another and the balloon maintains its coiled shape. For example, heat setting the coiled configuration of the balloon can include causing the outer surface of adjacent windings of the extruded tubing to adhere to one another via heating the tubing or the mandrel 1272. The extruding tubing can then be cooled to room temperature. In additional examples, adjacent windings may not be heat set in order to ensure that the windings remain laterally spaced from each other upon inflation.

Figure 13:
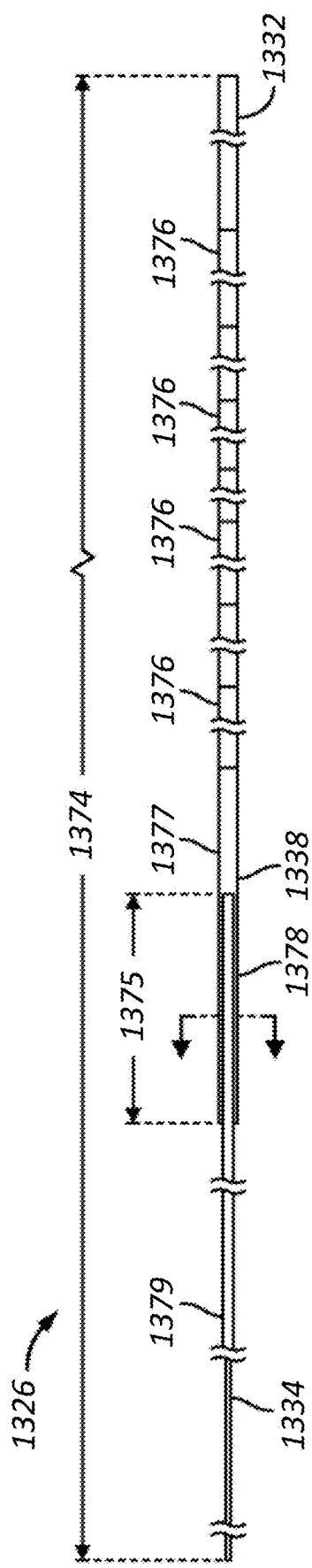
FIG. 13 illustrates a side view of an elongate shaft of a perfusion catheter, as constructed in accordance with at least one embodiment.
Figure 14:
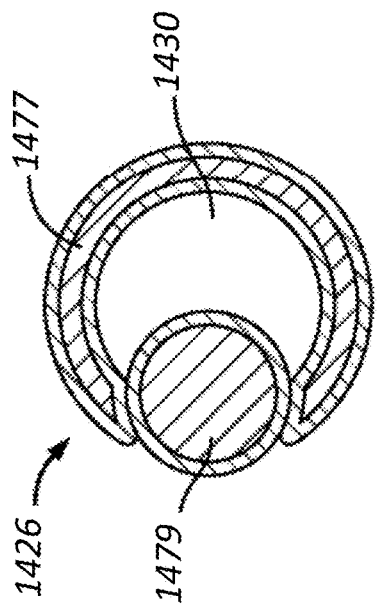
FIG. 14 illustrates a cross-sectional view of the elongate shaft shown in FIG. 13.

FIGS. 13 and 14 respectively illustrate side and cross-sectional views of an elongate shaft 1326, 1426 of a perfusion catheter, as constructed in accordance with at least one embodiment. The elongate shaft 1326, 1426 can include a lumen 1430 extending from a proximal portion 1332 to an inflation port for providing inflation fluid to, or withdrawing inflation fluid from, a distal (see FIG. 4) or proximal (see FIG. 7) end of a distal balloon. The elongate shaft 1326, 1426 can extend a length 1374 of 100 cm-200 cm and can possess the qualities of compression rigidity along its longitudinal axis, which facilitates advancement of the perfusion catheter through a patient's vascular system, and good distal flexibility, which enhances maneuverability of catheter through directional changes of the vascular system and prevents damage to the vessel walls as it is being inserted. Portions of the elongate shaft 1326, 1426 can include a PTFE coating 1376 to facilitate its advancement through the patient's vascular system.

These qualities are achievable in a variety of ways. In an example, proximal 1332 and intermediate 1338 portions of the elongate shaft 1326, 1426 can include a stainless steel hypotube 1377, 1477, and the distal portion 1334 can include a stainless steel support wire 1379, 1479 or tube that is connected for a length 1375 to the intermediate portion. The support wire 1379, 1479 can help transmit forces applied by a treating clinician to either advance or retract the balloon during a treatment procedure. The support wire 1379, 1479 can range in length from 10 cm-20 cm and can be secured to the hypotube 1377, 1477 via a laser weld. The support wire 1379, 1479 can extend to a location distal to the balloon or can terminate between the balloon's proximal and distal portions. In another embodiment, the elongate shaft 1326, 1426 can be formed from a single piece of metallic or polymer tubing with a proximal portion that has an outer and inner diameter larger than an outer and inner diameter of a distal portion or with a proximal portion having greater wall thickness than a distal portion.

A means to affix an outer surface 1378 of the elongate shaft 1326, 1426 and the flexible material of the balloon can be employed to withstand stresses associated with pressure changes of inflation and deflation of the balloon. It can be important that the affixing means create a fluid tight seal between the two materials and restrict any delamination along the seal line during prolonged periods of working pressures. In an example, portions of the elongate shaft 1326, 1426 coupled with the balloon can be covered with nylon (e.g., Vestamid L2101) as part of the affixing means.

The materials can be joined by an adhesive process, such as a cyanoacrylate, epoxy or urethane compounds, or joined by a heat treatment or pressure fit process that melts or welds the two materials together.

The perfusion catheters disclosed herein, along with the base layers and/or bioactive layers included thereon, may include, be coupled with, or embedded within a containment structure or sheath configured to shield the bioactive layer from physical shear forces and liquid solvents, e.g., blood, thereby reducing or at least postponing breakdown or release of the bioactive layer prior to reaching a treatment site. FIG. 15A illustrates such an example of a perfusion catheter 1500 including an inflatable balloon 1528 and a cylindrical containment structure 1580 surrounding the balloon. The containment structure 1580 can enclose and protect the balloon 1528, keeping the bioactive layer 1561 contained until it reaches the treatment site such that premature loss of one or more bioactive substances is minimized. In some examples, the containment structure 1580 can include or be integrally formed with the bioactive layer 1561. The containment structure 1580 can be flexible to accommodate inflation and deflation of the balloon 1528, such that an inner surface of the containment structure 1580 remains in contact with an outer surface of the inflatable balloon 1528 prior to, during, and after inflation. The outer surface of the containment structure 1580, which may press against an inner surface of a blood vessel wall at the treatment site, can be smooth to facilitate movement within a blood vessel. The containment structure 1580 may comprise a time-release structure formulated to dissolve or break down after a period of time, which preferably corresponds with the length of time necessary to reach a treatment site. In some examples, the containment structure 1580 is in the form of a sheath and may be removed upon arrival at the treatment site. After degradation or removal of the containment structure 1580, the inflatable balloon 1528 may remain positioned at the treatment site for an extended period of time, for example at least 60, 120, 180 seconds, or more, e.g., extending up to 5, 10, 15 minutes or more. During the residence time at the treatment site, the bioactive layer 1561 may continuously dissolve or otherwise breakdown, thereby releasing one or more bioactive substances therefrom, e.g., drugs, facilitated by one or more excipients. Because such substances are protected from early release by the containment structure 1580, greater amounts of the substances, e.g., higher doses, may be delivered to the treatment site.

FIG. 15B provides a cross-sectional view of the catheter 1500, showing the width of the containment structure 1580 and the bioactive layer 1561 positioned underneath. In additional examples, the bioactive layer 1561 may be incorporated within the containment structure 1580. According to such examples, the bioactive layer 1561 may constitute one layer of a multi-layered containment structure. For instance, the containment structure 1580 may comprise an outer layer or coating deposited on a dried, exterior surface of the bioactive layer 1561. According to such an example, the material(s) constituting the containment structure 1580 can be configured to dissolve or break down after a period of time, after which the underlying bioactive layer 1561 may be exposed and released. In additional examples, the bioactive layer 1561 may be sandwiched between an inner layer and an outer layer. The inner layer may be deposited on an outer surface of the inflatable balloon 1528, and the outer layer may be deposited on an exterior surface of the bioactive layer 1561. In yet another example, the containment structure 1580 may comprise a homogenous mixture of materials that includes the bioactive layer 1561, which can be defined as at least one drug and an excipient. The homogenous mixture may include one or more additional substances formulated to protect the bioactive layer materials from dissolving, at least for a period of time after insertion within a blood vessel.

FIG. 16 illustrates a catheter 1600 in accordance with another embodiment. As shown, the catheter 1600 includes a containment structure 1680 surrounding a portion of an inflated balloon 1628. Catheter 1600 can also include a bioactive layer or coating beneath the containment structure 1680. The containment structure 1680 in this example includes a plurality of radial struts 1682 interlaced with longitudinal struts 1684. The struts 1682, 1684 may be flexible to accommodate inflation and deflation of the balloon 1628, such that the struts remain in contact with an exterior surface of the balloon 1628 prior to, during, and after inflation.

Containment structures 1580 and 1680 provide only two examples of containment structure configurations that may be implemented in accordance with the methods and systems provided herein. For example, additional containment structures compatible with the perfusion catheters described herein can include a variety of stent devices, helically wound strands, perforated or non-perforated cylinders and/or dissolvable matrices, etc. The specific dimensions of the containment structure may vary, and may depend on the size and shape of the underlying inflatable balloon, the particular treatment being performed, and/or the size and configuration of the treatment site, e.g., within the coronary arteries, aorta and/or peripheral blood vessels. In some embodiments, perforated or porous containment structures may remain at the treatment site during bioactive layer dilution.

The materials constituting the containment structures 1580, 1680 can also vary. In embodiments, the materials can be biodegradable or non-biodegradable, elastic or inelastic, porous or non-porous. Example materials can include, but are not limited to, one or more of the following: stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxy-butyrate valerate or another biodegradable polymer, or mixtures or copolymers of these; a protein, an extracellular matrix component, collagen, fibrin or another biologic agent.

FIG. 17 illustrates a method 1700 of using a perfusion catheter in a coronary vessel for treating a tissue abnormality, e.g., treating a lesion, sealing a perforation or dissection, and/or dilating occlusive material while maintaining a passage and delivering a bioactive substance.

At 1782, the method may involve passing a perfusion catheter, including a balloon, an elongate shaft that is attached to the balloon, and a containment structure surrounding at least a portion of the balloon, into a blood vessel until the balloon is positioned adjacent a lesion. In some examples, the containment structure may be a protective tube, sheath or guide catheter, that is coupled with but removable from the rest of the perfusion catheter after reaching a targeted treatment site. In other examples, the containment structure may involve degradation of the containment structure from the balloon after reaching the targeted treatment site.

At 1784, the method may involve inflating the balloon until an outer surface of the balloon contacts an inner surface of the blood vessel by urging fluid through a lumen of the elongate shaft and into the balloon.

At 1786, the method may involve the balloon, upon inflation, moving from a deflated configuration to an inflated configuration at which an outer surface of the containment structure engages the wall of the blood vessel. As mentioned above, the containment structure may be excluded in some embodiments. According to such embodiments, an outer surface of the balloon and/or any additional coatings or layers included thereon, such as a base layer and/or bioactive layer, may instead engage the wall of the blood vessel.

At 1788, the method may involve maintaining the balloon in the inflated configuration at the lesion during removal of the containment structure and release of a bioactive layer into the wall of the blood vessel. In some examples, the bioactive layer may be excluded. Such examples may release one or more treatment substances from within an inner lumen of the helical windings of the balloon, for example by emitting the treatment substances through a plurality of perforations or holes defined by at least a subset of the helical windings.

Figure 18:
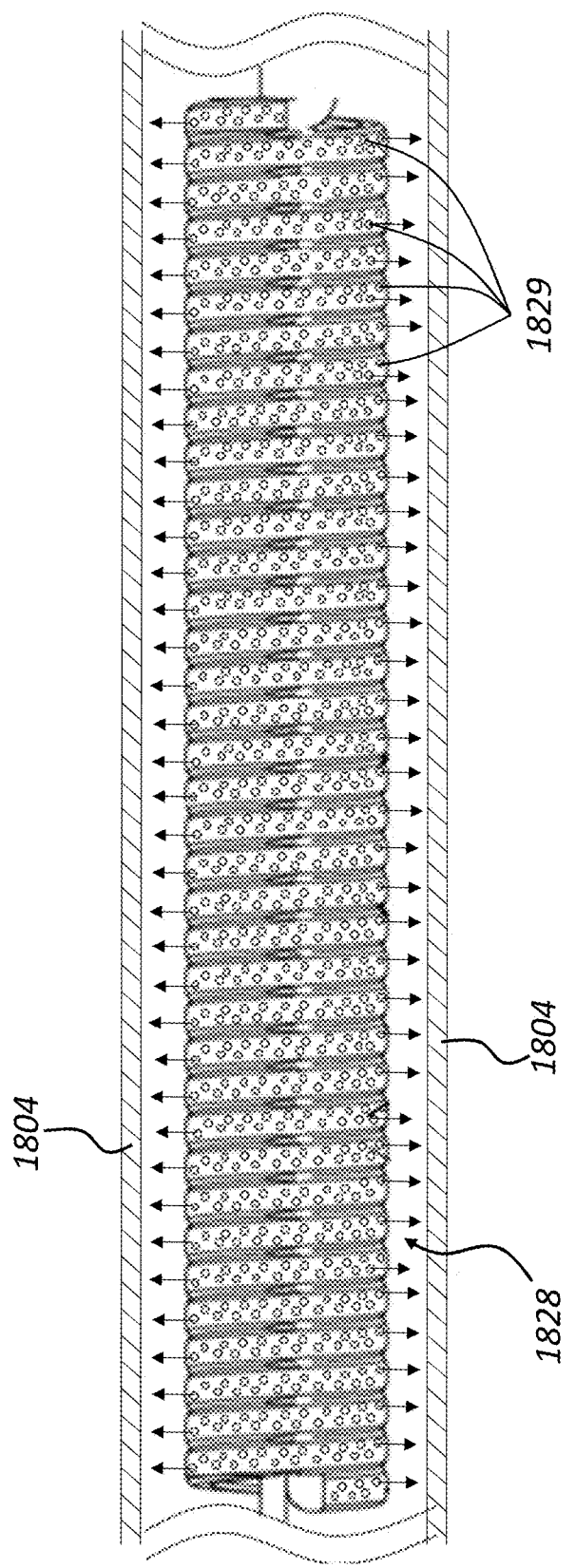
FIG. 18 illustrates an enlarged side view of another inflated balloon included with a perfusion catheter, as constructed in accordance with at least one embodiment.

In some embodiments, a perfusion balloon, such as balloon 428 or 1628, may be configured to infuse a bioactive substance, e.g., a drug or treatment substance, directly into a vessel, for example by releasing or spraying the drug from small holes or passageways in the balloon. An example of such a device is shown in FIG. 18, which illustrates an inflatable balloon 1828 that may be included on a perfusion catheter in accordance with embodiments disclosed herein. As shown, the inflatable balloon 1828 defines a plurality of holes 1829 configured to release a treatment substance directly into a blood vessel wall 1804 in the direction of the arrows. Methods of forming and operating such balloons may vary. In embodiments, one or more holes could be formed in a coiled balloon, which may be inflated from the catheter's proximal end using the liquid form of a drug, for example.

FIG. 19 illustrates an enlarged side view of another inflated balloon 1928 configured to infuse a bioactive substance, e.g., a drug or treatment substance, directly into a vessel. The balloon 1928 is comprised of two separate windings or filars interwoven in an alternating manner, each filar comprising a separate, distinct lumen. The first filar may comprise an inflation filar 1966 and the second may comprise an elution filar 1968. The inflation filar 1966 is configured to inflate and secure the balloon 1928 within a blood vessel at or upstream of a treatment site in a manner consistent with the embodiments described herein. The elution filar 1968 is configured to elute a bioactive substance, e.g., one or more drugs, therapeutic agents, diagnostic agents, or combinations thereof. To release the bioactive substance, the elution filar 1968 may define a plurality of perforations or holes 1970. Bioactive substances forced through the elution filar 1968 may thus exit the elution filar by passing through the holes 1970. The holes 1970 may be distributed throughout a distal portion of the elution filar 1968, covering the entire balloon 1928 or at least a portion thereof. The number, size and configuration of the holes 1970 may vary, such that the elution filar 1968 may be generally porous in some embodiments. The dimensions of the holes 1970 may vary depending on the desired elution rate. For example, for operations requiring a slow elution rate, the holes 1970 may be small in diameter such that the treatment substance is "misted" out from the elution filar 1968. Embodiments configured to elute a treatment substance outwardly from the elution filar 1968, such as the example shown in FIG. 19, may not include a bioactive layer or coating surrounding an external surface of the balloon 1928.

The winding diameters of the inflation filar 1966 and the elution filar 1968 may be the same or different. FIG. 20 illustrates an enlarged side view of an inflated balloon 2028 comprised of an alternating inflation filar 2066 and an elution filar 2068, in which the elution filar 2068 comprises a more narrow outer diameter than the inflation filar 2066. In this embodiment, the inflation filar 2066 defines a wider outer diameter such that it is configured to hold the balloon 2028, and thus the entire perfusion catheter, in place while the elution filar 2068 releases the bioactive substance. As shown, the inflation filar 2068 may again define a plurality of perforations or holes 2070 to facilitate release of the bioactive substance directly into the vessel.

In some examples, the elution filar 1968, 2068 may be configured to elute the treatment substance from an inner surface of the helical windings. According to such examples, the elution filar 1968, 2068 may define a plurality of perforations or holes along the inner surface, only, of the filar. In this manner, the bioactive substance is released within the internal passage, e.g., internal passage 644, defined by the balloon 1928, 2028 after inflation. Embodiments configured to release the bioactive substance inwardly, i.e., into the internal passageway defined by the inflated balloon, may be particularly well suited for delivery drugs, e.g., chemotherapeutics, or drug concentrations that may harm, e.g., burn, a vessel wall if directly applied thereto. The blood flowing through the internal passage will dilute such substances, thereby reducing the likelihood of harming a vessel wall at or downstream of the target site.

FIG. 21 provides a cross-sectional view of a catheter 2100 coupled with a protective guide catheter, tube, or sheath 2182. The sheath 2182 can comprise an elongate tube member defining a main lumen 2184 along its length. The sheath 2182 can be formed of polyurethane, for example, or of other suitable materials. As shown, the protective sheath 2182 may surround the inflatable balloon 2128 and optional bioactive layer 2161 applied thereon. The sheath 2182 can enclose and protect the balloon 2128, keeping the bioactive layer 2161 contained until it reaches the treatment site such that premature loss of one or more bioactive substances is reduced or minimized. The outer surface of the sheath 2182, which may press against an inner surface of a blood vessel wall, can be smooth to facilitate movement within a blood vessel. The sheath 2182 can be used to guide the catheter 2100 to the treatment site, while protecting the catheter from damage. After reaching the treatment site, the sheath 2182 may be removed from the blood vessel, or retracted away from the treatment site.

Figure 22:
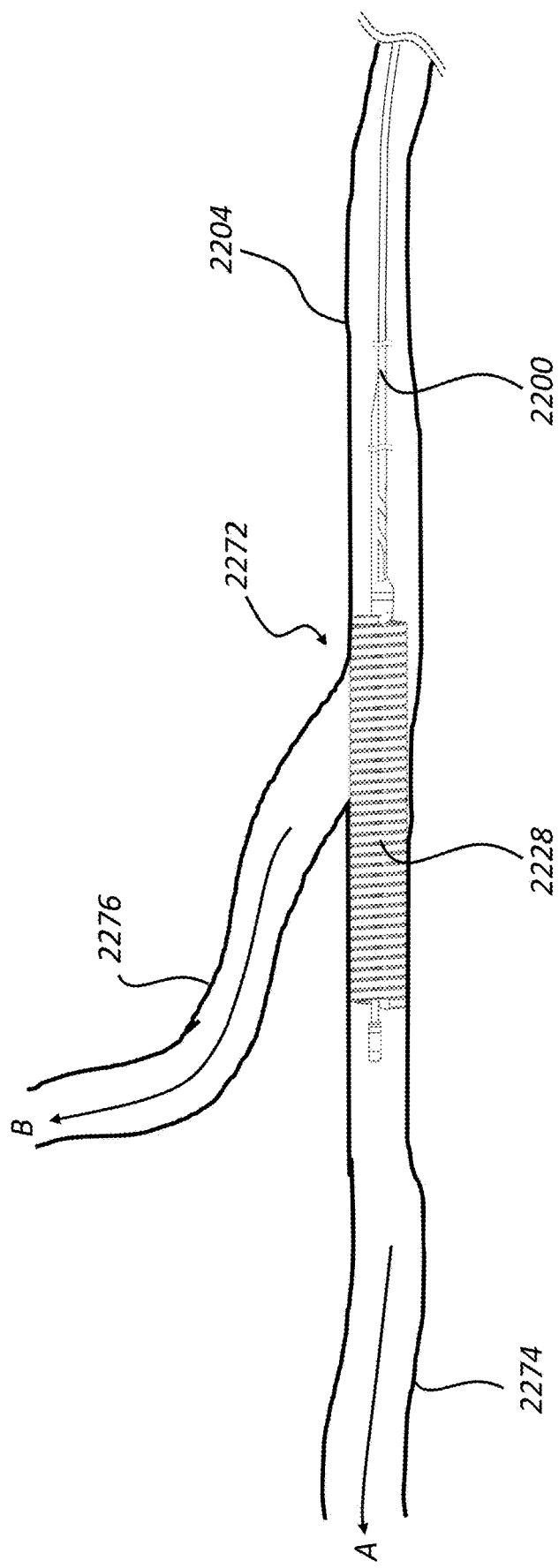
FIG. 22 illustrates a schematic view of a distal portion of a perfusion catheter positioned at a vessel bifurcation.

As further shown in FIG. 22, methods of using the perfusion catheters disclosed herein may involve selectively positioning the balloon at a vessel bifurcation. Specifically, a perfusion catheter 2200 may be positioned at a vessel bifurcation 2272 such that the balloon 2228, after inflation, releases a bioactive substance, either from a bioactive layer, an elution filar or otherwise, down one vessel branch 2274 but not the other branch 2276. In this manner, the treatment substance is released down path A, which may lead to or include the targeted treatment site, but not down path B.

CLOSING NOTES

The above Detailed Description includes references to the accompanying drawings, which form a part of the Detailed Description. The Detailed Description should be read with reference to the drawings. The drawings show, by way of illustration, specific embodiments in which the present catheters and related methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Various features or components have been grouped together to streamline the disclosure. This should not be interpreted as intending that an unclaimed disclosed feature, component or grouping is essential to any claim. Rather, inventive subject matter can lie in less than all features, components or groupings of a particular disclosed embodiment. Thus, the following claim examples are hereby incorporated into the Detailed Description, with each example standing on its own as a separate embodiment:

In a first example, a method may involve passing a perfusion catheter, including a balloon and an elongate shaft that is operably attached to the balloon, into a blood vessel until the balloon is positioned adjacent a lesion or abnormality in a wall of the blood vessel. The balloon can be configured to release one or more substances formulated to treat a tissue at or near the wall of the blood vessel. The method may also involve inflating the balloon to engage an inner surface of the wall of the blood vessel, such as by urging fluid through a lumen of the elongate shaft and into the balloon to inflate a series of helical windings of the balloon. The balloon, upon inflation, moves from a deflated configuration to an inflated configuration at which an outer surface of the balloon engages the wall of the blood vessel and an inner surface of the balloon's series of helical windings defines a passage for blood to flow. The method may further involve maintaining the balloon in the inflated configuration at the lesion or abnormality during release of the one or more substances into the wall of the blood vessel. In some examples, maintaining the balloon in the inflated configuration can involve maintaining the balloon in the inflated configuration for greater than 60 seconds.

In some examples, the perfusion catheter further includes a bioactive layer coating an outer surface of the balloon. The bioactive layer can include the one or more substances formulated to treat the tissue at or near the wall of the blood vessel. In some examples, the one or more substances include one or more drugs, therapeutic agents, diagnostic agents, or combinations thereof. In some examples, the bioactive layer includes one or more drugs and one or more excipients. According to such examples, the one or more excipients include an antioxidant, urea, propyl gallate, a hydrophilic additive, or combinations thereof.

In some examples, the perfusion catheter further includes a containment structure surrounding at least a portion of the bioactive layer. Such examples may further involve removing the containment structure before release of the bioactive layer into the wall of the blood vessel. Removal of the containment structure may involve degradation of the containment structure. In some examples, the containment structure includes a biodegradable material, which may include or comprise a time-release material. In some examples, removal of the containment structure can involve extraction of the containment structure from the blood vessel in a distal-to-proximal direction. In some examples, the containment structure comprises a protective sheath, tube or guide catheter. In some embodiments, the containment structure comprises a flexible material configured to expand upon inflation of the balloon.

In some examples, the perfusion catheter further includes a base layer positioned between the outer surface of the balloon and the bioactive layer. The base layer can be configured to provide a smooth foundation over the series of helical windings of the balloon. The base layer may include one or more excipients.

In some examples, the balloon can comprise two or more filars interwoven in an alternating manner. The two or more filars can include an inflation filar and an elution filar. The inflation filar can be configured to engage the wall of the blood vessel, and the elution filar can be configured to release the one or more substances. In some examples, the elution filar defines a plurality of perforations or holes positioned and configured to release the one or more substances from an interior lumen of the elution filar. In some examples, the plurality of perforation or holes are positioned and configured to release the one or more substances within the passage defined by the balloon.

In accordance with one or more of the aforementioned examples, passing the perfusion catheter into the blood vessel can include advancing a guidewire through a guidewire support tube, which is separate from the lumen of the elongate shaft and the passage defined by the balloon. In some examples, passing the perfusion catheter into the blood vessel can include advancing a guidewire through a guidewire support tube, which is inset into the inner surface of the balloon's series of helical windings. In some examples, inflating the balloon involves dilating occlusive material accumulation within the wall of the blood vessel. In some examples, inflating the balloon comprises urging fluid into the balloon in a distal-to-proximal direction of the balloon. In some examples, inflating the balloon includes inflating the balloon to a pressure between 2 atm-20 atm, inclusive. In some examples, maintaining the balloon in the inflated configuration comprises maintaining the balloon in the inflated configuration for between 60 seconds and 15 minutes. In some examples, passing the perfusion catheter into the blood vessel further comprises stopping the balloon at a vessel bifurcation, such that of the two blood vessels at the vessel bifurcation, the one or more substances are released exclusively within one of the blood vessels.

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
passing a perfusion catheter assembly, including a balloon including two or more adjacent filars interwoven in an alternating manner and an elongate shaft that is operably attached to the balloon, into a blood vessel until the balloon is positioned adjacent a lesion or abnormality in a wall of the blood vessel, wherein the two or more adjacent filars have an inner surface diameter of a same size that collectively define an inner surface of the balloon, and wherein the balloon is configured to release one or more substances formulated to treat a tissue at or near the wall of the blood vessel;
inflating the balloon, including moving the balloon from a deflated configuration to an inflated configuration at which an outer surface of the balloon engages the wall of the blood vessel and the inner surface of the balloon defines a passage for bodily fluid to flow; and
maintaining the balloon in the inflated configuration at the lesion or abnormality during release of the one or more substances into the wall of the blood vessel.

2. The method of claim 1, wherein maintaining the balloon in the inflated configuration comprises maintaining the balloon in the inflated configuration for greater than 60 seconds.

3. The method of claim 1, wherein maintaining the balloon in the inflated configuration comprises maintaining the balloon in the inflated configuration for between 60 seconds and 15 minutes.

4. The method of claim 1, wherein inflating the balloon comprises urging a fluid into the balloon in a distal-to-proximal direction of the balloon.

5. The method of claim 1, wherein the perfusion catheter assembly further comprises a bioactive layer coating one or more portions of the outer surface of the balloon, the bioactive layer including the one or more substances formulated to treat the tissue at or near the wall of the blood vessel.

6. The method of claim 5, the one or more substances consisting of one or more drugs, therapeutic agents, diagnostic agents, excipients, or combinations thereof.

7. The method of claim 6, the one or more excipients consisting of an antioxidant, urea, propyl gallate, a hydrophilic additive, or combinations thereof.

8. The method of claim 5, wherein the perfusion catheter assembly further comprises a containment structure surrounding at least a portion of the bioactive layer.

9. The method of claim 8, further comprising removing the containment structure before release of the bioactive layer into the wall of the blood vessel.

10. The method of claim 9, wherein removing the containment structure comprises degradation of the containment structure.

11. The method of claim 9, wherein removing the containment structure comprises extraction of the containment structure from the blood vessel in a distal-to-proximal direction.

12. The method of claim 11, wherein the containment structure comprises a protective sheath.

13. The method of claim 5, wherein inflating the balloon comprises urging fluid into the balloon to inflate a series of helical windings of the balloon.

14. The method of claim 13, wherein the perfusion catheter assembly further comprises a base layer positioned between the outer surface of the balloon and the bioactive layer, the base layer configured to provide a smooth foundation over the series of helical windings of the balloon.

15. The method of claim 1, wherein passing the perfusion catheter assembly into the blood vessel further comprises positioning the balloon at a vessel bifurcation, such that of two blood vessels at the vessel bifurcation, the one or more substances are released exclusively within one of the blood vessels.

16. A method, comprising:
passing a perfusion catheter assembly, including a balloon including two or more interwoven filars and an elongate shaft that is operably attached to the balloon, into a blood vessel until the balloon is positioned adjacent a lesion or abnormality in a wall of the blood vessel, wherein the balloon is configured to release one or more substances formulated to treat a tissue at or near the wall of the blood vessel, and wherein the two or more interwoven filars include an inflation filar configured to engage the wall of the blood vessel and an elution filar configured to release the one or more substances;
inflating the balloon, including moving the balloon from a deflated configuration to an inflated configuration at which an outer surface of the balloon engages the wall of the blood vessel and an inner surface of the balloon defines a passage for bodily fluid to flow; and
maintaining the balloon in the inflated configuration at the lesion or abnormality during release of the one or more substances into the wall of the blood vessel.

17. The method of claim 16, wherein the elution filar defines a plurality of perforations or holes positioned and configured to release the one or more substances from a lumen of the elution filar.

18. The method of claim 17, wherein the plurality of perforations or holes are positioned and configured to release the one or more substances within the passage defined by the balloon.

19. The method of claim 18, further comprising diluting the one or more substances with flowing bodily fluid prior to being received into the wall of the blood vessel.

20. The method of claim 17, wherein the plurality of perforations or holes are positioned and configured to release the one or more substances directly into the wall of the blood vessel.

\* \* \* \* \*

UNITED STATES PATENT AND TRADEMARK OFFICE
CERTIFICATE OF CORRECTION

| | | |
|---|---|---|
| PATENT NO. | : 11,511,086 B2 | Page 1 of 1 |
| APPLICATION NO. | : 16/540844 | |
| DATED | : November 29, 2022 | |
| INVENTOR(S) | : Bridgeman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this
Eleventh Day of February, 2025

Coke Morgan Stewart
*Acting Director of the United States Patent and Trademark Office*